(12) United States Patent
Togashi et al.

(10) Patent No.: US 8,435,749 B2
(45) Date of Patent: May 7, 2013

(54) ANTI-CDH3 ANTIBODIES LABELED WITH RADIOISOTOPE LABEL AND USES THEREOF

(75) Inventors: Akira Togashi, Kanagawa (JP); Masakazu Katsu, Kanagawa (JP); Megumi Takayanagi, Kanagawa (JP); Hiroki Yoshioka, Kanagawa (JP); Pohsing Ng, Kanagawa (JP); Yasuhiro Shiba, Kanagawa (JP); Yusuke Nakamura, Tokyo (JP); Keigo Endo, Gunma (JP)

(73) Assignee: Oncotherapy Science, Inc., Kanagawa (JP)

( * ) Notice: Subject to any disclaimer, the term of this patent is extended or adjusted under 35 U.S.C. 154(b) by 85 days.

(21) Appl. No.: 13/001,869

(22) PCT Filed: Jun. 30, 2009

(86) PCT No.: PCT/JP2009/003009
§ 371 (c)(1),
(2), (4) Date: Mar. 31, 2011

(87) PCT Pub. No.: WO2010/001585
PCT Pub. Date: Jan. 7, 2010

(65) Prior Publication Data
US 2012/0128584 A1    May 24, 2012

Related U.S. Application Data

(60) Provisional application No. 61/076,982, filed on Jun. 30, 2008.

(51) Int. Cl.
| | |
|---|---|
| *G01N 33/53* | (2006.01) |
| *A61K 39/395* | (2006.01) |
| *C07K 16/00* | (2006.01) |
| *C07K 16/28* | (2006.01) |

(52) U.S. Cl.
USPC ... 435/7.1; 424/130.1; 424/143.1; 424/155.1; 530/387.1; 530/388.22

(58) Field of Classification Search .................. None
See application file for complete search history.

(56) References Cited

U.S. PATENT DOCUMENTS

| | | |
|---|---|---|
| 2005/0214836 A1 | 9/2005 | Nakamura et al. |
| 2005/0260639 A1 | 11/2005 | Nakamura et al. |
| 2006/0024692 A1 | 2/2006 | Nakamura et al. |
| 2006/0105333 A1 | 5/2006 | Nakamura et al. |
| 2006/0194199 A1 | 8/2006 | Nakamura et al. |
| 2006/0199179 A1 | 9/2006 | Nakamura et al. |
| 2006/0246077 A1* | 11/2006 | Bar-Eli et al. .............. 424/155.1 |
| 2009/0162361 A1 | 6/2009 | Nakamura et al. |
| 2009/0169572 A1 | 7/2009 | Nakatsuru et al. |
| 2009/0175844 A1 | 7/2009 | Nakamura et al. |
| 2010/0040641 A1 | 2/2010 | Tsunoda et al. |
| 2012/0014996 A1 | 1/2012 | Nakamura et al. |

FOREIGN PATENT DOCUMENTS

| | | |
|---|---|---|
| EP | 1830187 A1 | 9/2007 |
| NL | 1031818 C2 | 11/2007 |
| WO | WO 02/097395 A2 | 12/2002 |
| WO | WO 04/001072 A2 | 12/2003 |
| WO | WO 2004/007770 A2 | 1/2004 |
| WO | WO 2004/024952 A1 | 3/2004 |
| WO | WO 2004/031410 A2 | 4/2004 |
| WO | WO 2004/031412 A2 | 4/2004 |
| WO | WO 2004/031413 A2 | 4/2004 |
| WO | WO 2004/110345 A2 | 12/2004 |
| WO | WO 2005/090572 A2 | 9/2005 |
| WO | WO 2006/085684 A2 | 8/2006 |
| WO | WO 2006/114704 A2 | 11/2006 |
| WO | 2007/075672 A2 | 7/2007 |
| WO | WO 2007/102525 A1 | 9/2007 |
| WO | WO 2008/102557 A1 | 8/2008 |
| WO | WO 2009/025116 A1 | 2/2009 |

OTHER PUBLICATIONS

Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Baselga, J., "Herceptin® Alone or in Combination with Chemotherapy in the Treatment of HER2-Positive Metastatic Breast Cancer: Pivotal Trials," *Oncology*, vol. 61, Suppl. 2, pp. 14-21 (2001).
Behrens, J., et al., "Cadherins and catenins: Role in signal transduction and tumor progression," *Cancer and Metastasis Reviews*, vol. (1). 18, pp. 15-30 (1999).
Conacci-Sorrell, M., et al., "The cadherin-catenin adhesion system in signaling and cancer," *The Journal of Clinical Investigation*, vol. 109(8), pp. 987-991 (Apr. 2002).
Crist, W., et al., "Intergroup Rhabdomyosarcoma Study-IV: Results for Patients With Nonmetastatic Disease," *Journal of Clinical Oncology*, vol. 19(12), pp. 3091-3102 (Jun. 2001).
Daniel, C., et al., "Expression and Functional Role of E-and P-Cadherins in Mouse Mammary Ductal Morphogenesis and Growth," *Dev. Biol.*, vol. 169(2), pp. 511-519 (Jun. 1995).
Ferguson, W., et al., "Current Treatment of Osteosarcoma," *Cancer Investigation*, vol. 19(3), pp. 292-315 (2001).
Ferrara, N., et al., "Discovery and Development of Bevacizumab, an Anti-VEGF Antibody for Treatment Cancer," *Nat Rev Drug Discov.*, vol. 3(5), pp. 391-400 (May 2004).
Gamallo, C., et al., "The Prognostic Significance of P-Cadherin in Infiltrating Ductal Breast Carcinoma," *Mod Pathol.*, vol. 14(7), pp. 650-654 (Jul. 2001).
Harris, M., "Monoclonal antibodies as therapeutic agents for cancer," *Lancet Oncol.*, vol. 5(5), pp. 292-302 (May 2004).

(Continued)

*Primary Examiner* — Maher Haddad
(74) *Attorney, Agent, or Firm* — Kilpatrick Townsend & Stockton LLP

(57) ABSTRACT

The present invention relates to anti-CDH3 antibodies, which can be labeled with a radioisotope. Moreover, the present invention provides methods and pharmaceutical compositions that comprise an anti-CDH3 antibody as an active ingredient. Since CDH3 is strongly expressed in pancreatic, lung, colon, prostate, breast, gastric or liver cancer cells, the present invention is useful in pancreatic, lung, colon, prostate, breast, gastric or liver cancer therapies.

16 Claims, 11 Drawing Sheets

OTHER PUBLICATIONS

Maloney, D., et al., "IDEC-C2B8 (Rituximab) Anti-CD20 Monoclonal Antibody Therapy in Patients With Relapsed Low-Grade Non-Hodgkin's Lymphoma," *Blood*, vol. 90(6), pp. 2188-2195 (Sep. 15, 1997).

Nakamura, T., et al., "Genome-wide cDNA microarray analysis of gene expression profiles in pancreatic cancers using populations of tumor cells and normal ductal epithelial cells selected for purity by laser microdissection," *Oncogene*, vol. 23(13), pp. 2385-2400 (Mar. 25, 2004).

Nose, A., et al. "A Novel Cadherin Cell Adhesion Molecule: Its Expression Patterns Associated with Implantation and Organogenesis of Mouse Embryos," *J Cell Biol.*, vol. 103(6, Pt. 2), pp. 2649-2658 (Dec. 1986).

Nose, A., et al., "Expressed Recombinant Cadherins Mediate Cell Sorting in Model Systems," *Cell*, vol. 54(7), pp. 993-1001 (Sep. 23, 1988).

Shimoyama, Y., et al., "Cadherin Cell-Adhesion Molecules in Human Epithelial Tissues and Carcinomas," *Cancer Res.*, vol. 49(8), pp. 2128-2133 (Apr. 15, 1989).

Stefansson, I., et al., Prognostic Impact of Alterations in P-Cadherin Expression and Related Cell Adhesion Markers in Endometrial Cancer, *J Clin Oncol.*, vol. 22(7), pp. 1242-1252 (Apr. 1, 2004).

Steinberg, M., et al., "Experimental specification of cell sorting, tissue spreading, and specific spatial patterning by quantitative differences in cadherin expression," *Proc Natl Acad Sci USA.* vol. 91(1), pp. 206-209 (Jan. 4, 1994).

Takeichi, M., "The cadherins: cell-cell adhesion molecules controlling animal morphogenesis," *Development*, vol. 102(4), pp. 639-655 (Apr. 1988).

Takeichi, M., "Cadherin Cell Adhesion Receptors as a Morphogenetic Regulator," *Science*, vol. 251(5000), pp. 1451-1455 (Mar. 22, 1991).

Wunder, J., et al., "The Histological Response to Chemotherapy as a Predictor of the Oncological Outcome of Operative Treatment of Ewing Sarcoma," *J Bone Joint Surg Am*, vol. 80(7), pp. 1020-1033 (Jul. 1998).

U.S. Appl. No. 12/673,451, filed Jun. 5, 2008, 134 pgs.

U.S. Appl. No. 13/464,831, filed May 4, 2012, 163 pages.

U.S. Appl. No. 13/536,327, 204 pages, filed Jun. 28, 2012.

U.S. Appl. No. 13/519,127, which is a U.S. National Stage of PCT/JP2009/007333, 59 pages, filed Dec. 28, 2009.

Mialhe, et al., "Expression of E-, P-, N-Cadherins and Catenins in Human Bladder Carcinoma Cell Lines," *J Urol.*, vol. 164(3 Pt 1), pp. 826-835 (Sep. 2000).

Pyo, et al., "Expression of E-cadherin, P-cadherin and N-cadherin in oral squamous cell carcinoma: Correlation with the clinicopathologic features and patient outcome," *J Craniomaxillofac Surg.*, vol. 35(1), pp. 1-9 (Epub Feb. 12, 2007, Jan. 2007).

Wu, et al., "JNK signaling pathway is required for bFGF-mediated surface cadherin downregulation on HUVEC," *Exp Cell Res.*, vol. 314(3), pp. 421-429, doi: 10. 1016/j.yexcr (Epub Oct. 6, 2007, Feb. 1, 2008).

U.S. Appl. No. 13/744,354, filed Jan. 17, 2013, 124 pages.

Supplementary European Search Report for European Application EP 09773163, dated Dec. 7, 2012, 4 pages.

* cited by examiner

Fig. 1
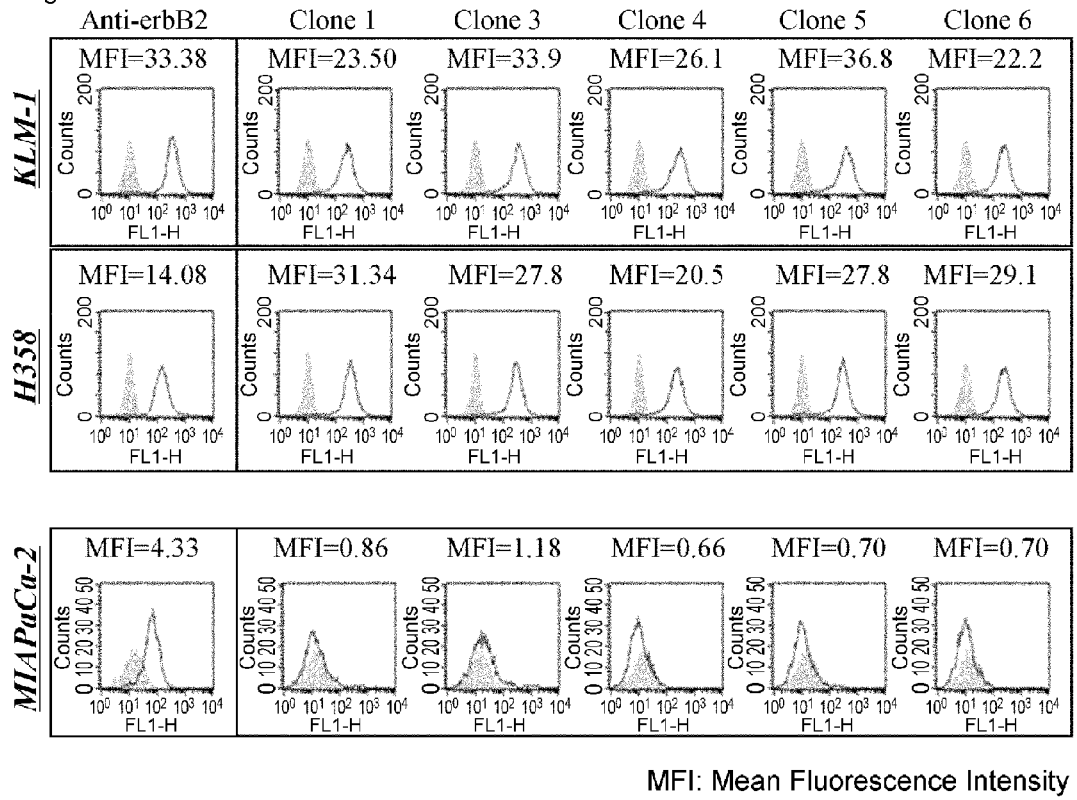
MFI: Mean Fluorescence Intensity
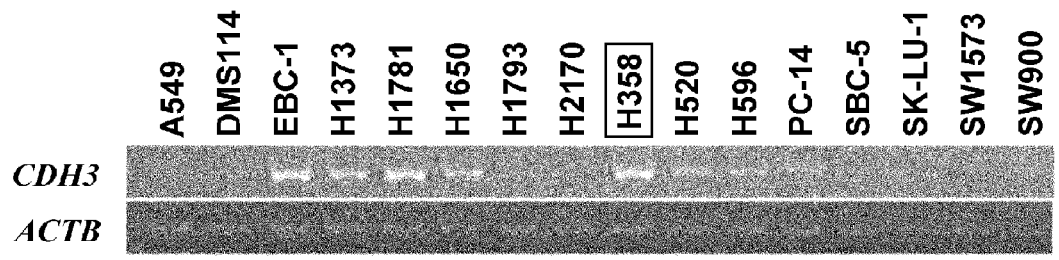
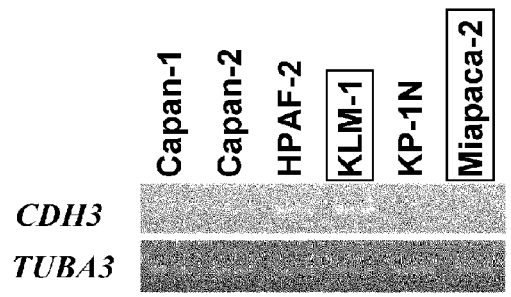

Fig. 2A-B
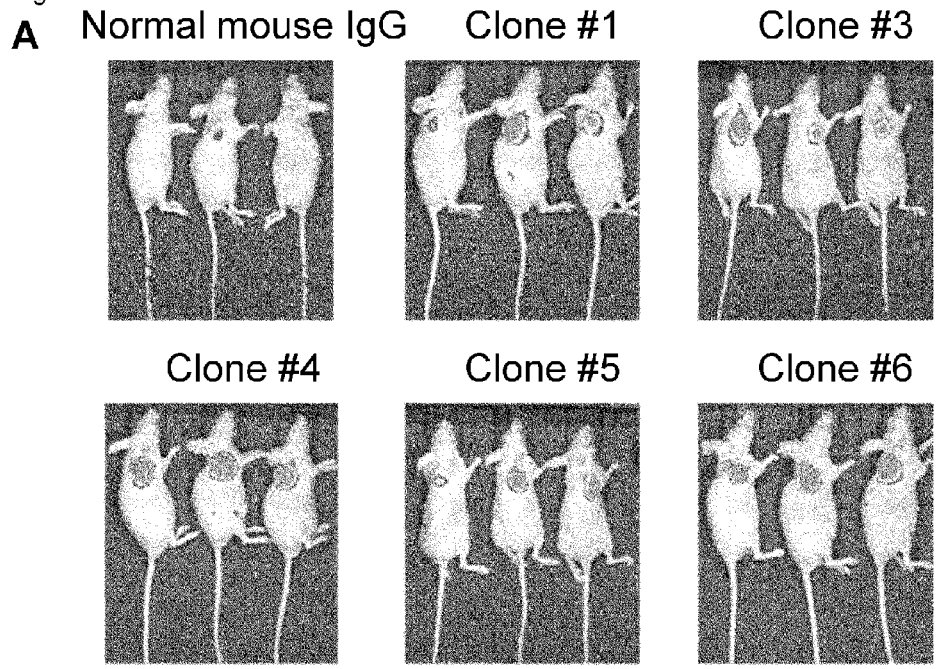
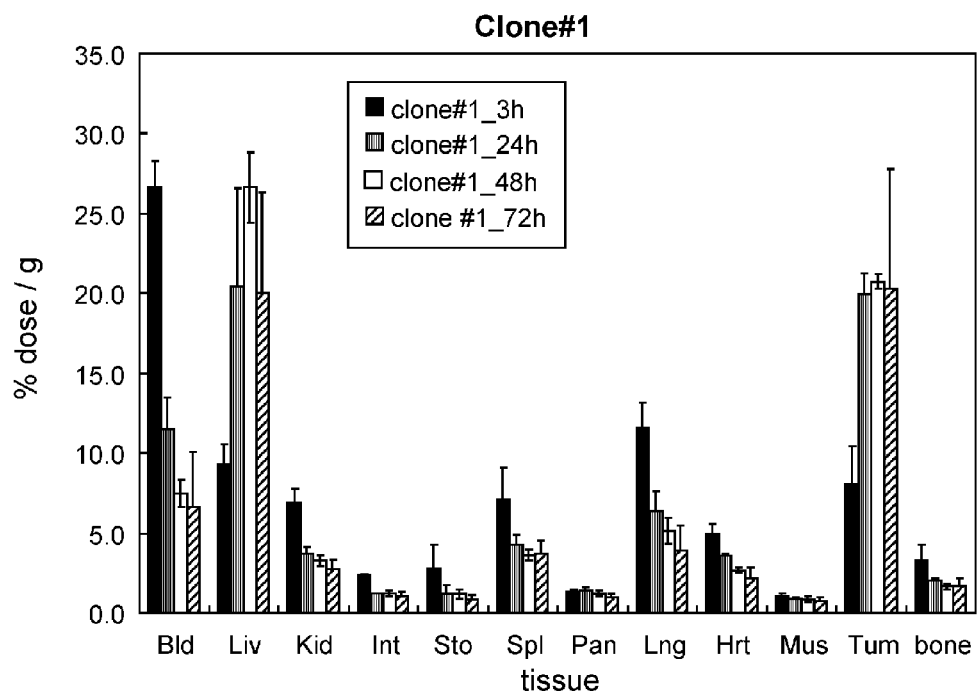

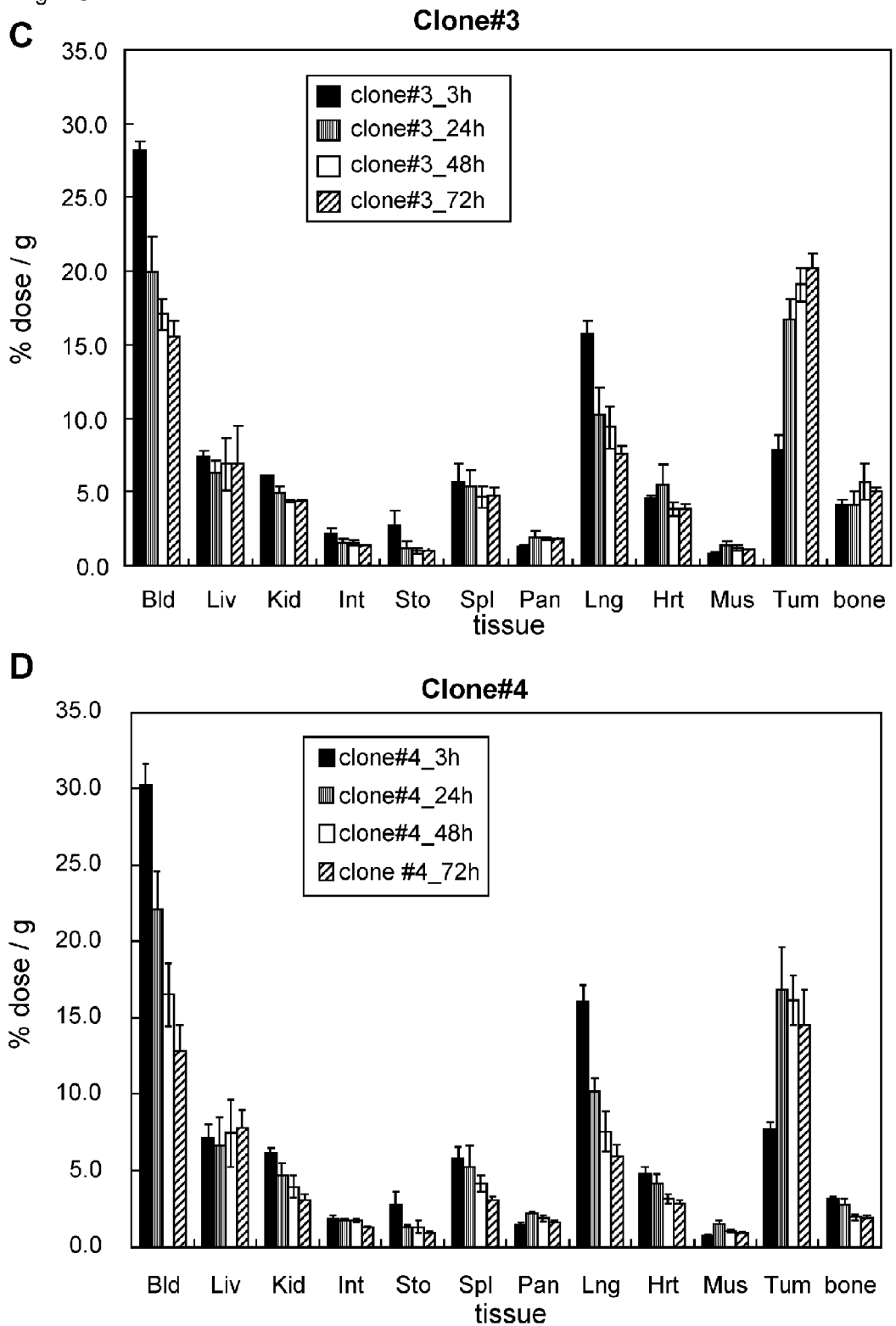
Fig. 2C-D

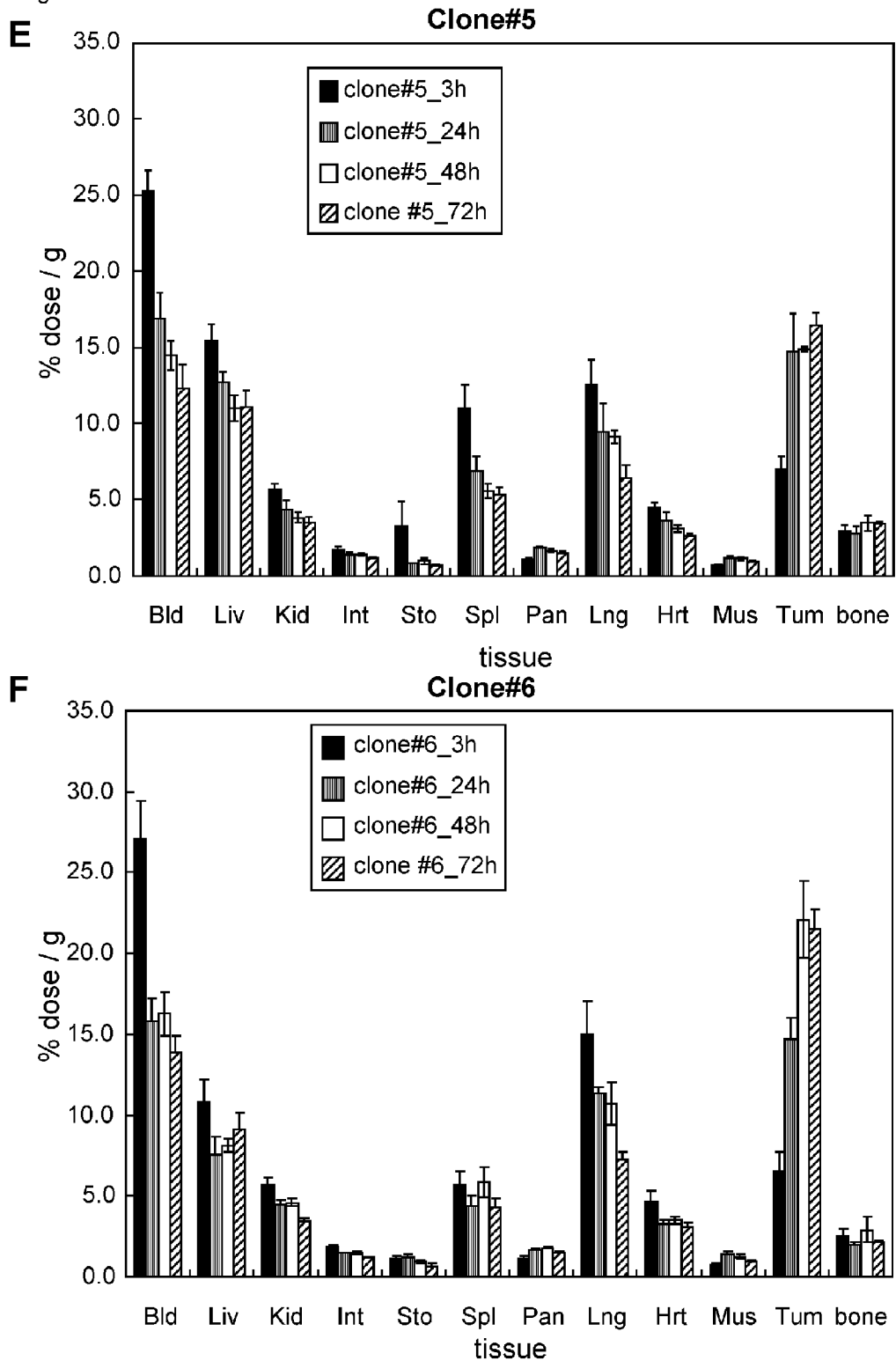
Fig. 2E-F

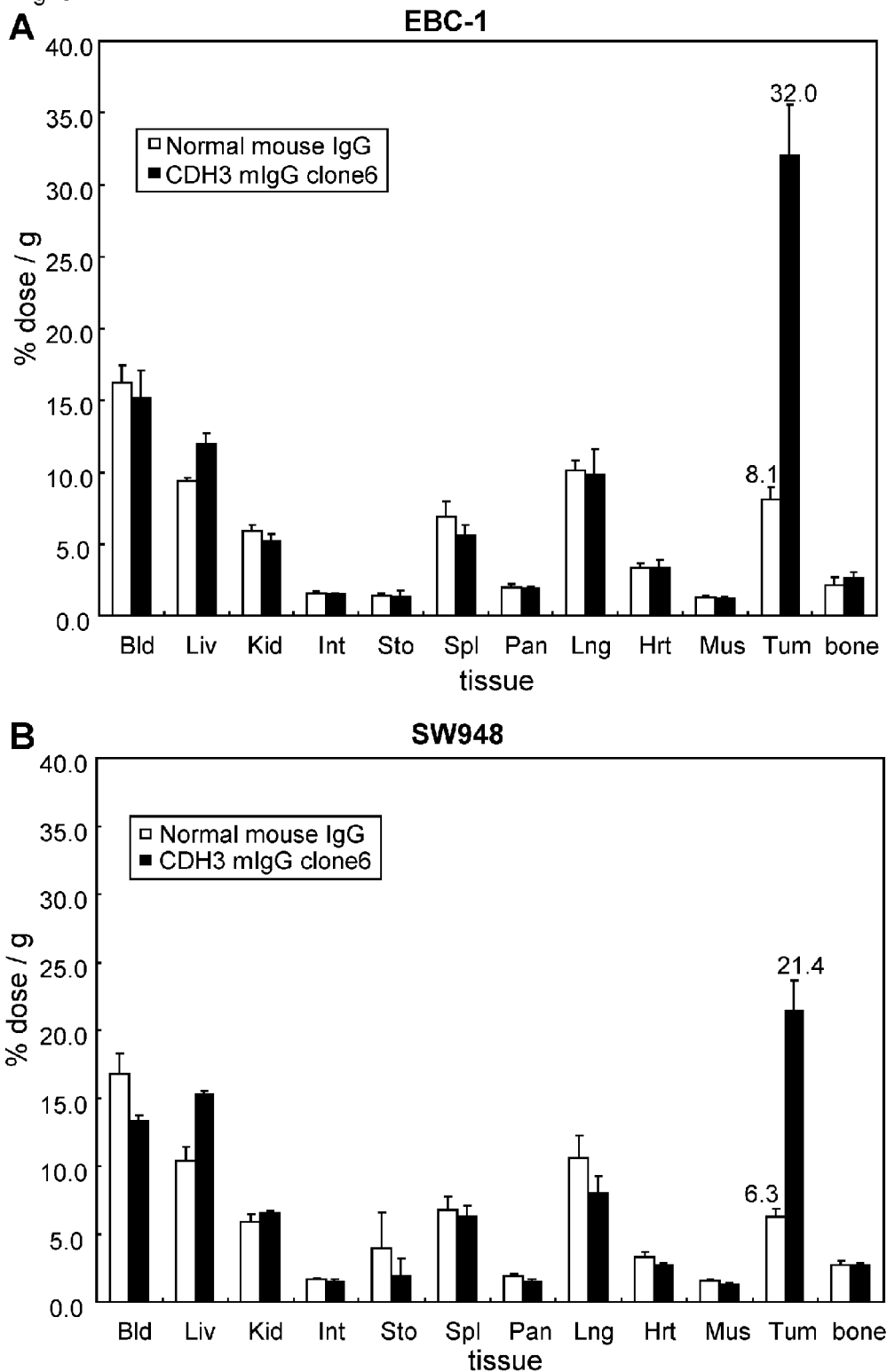
Fig. 3A-B

Fig. 3C-D
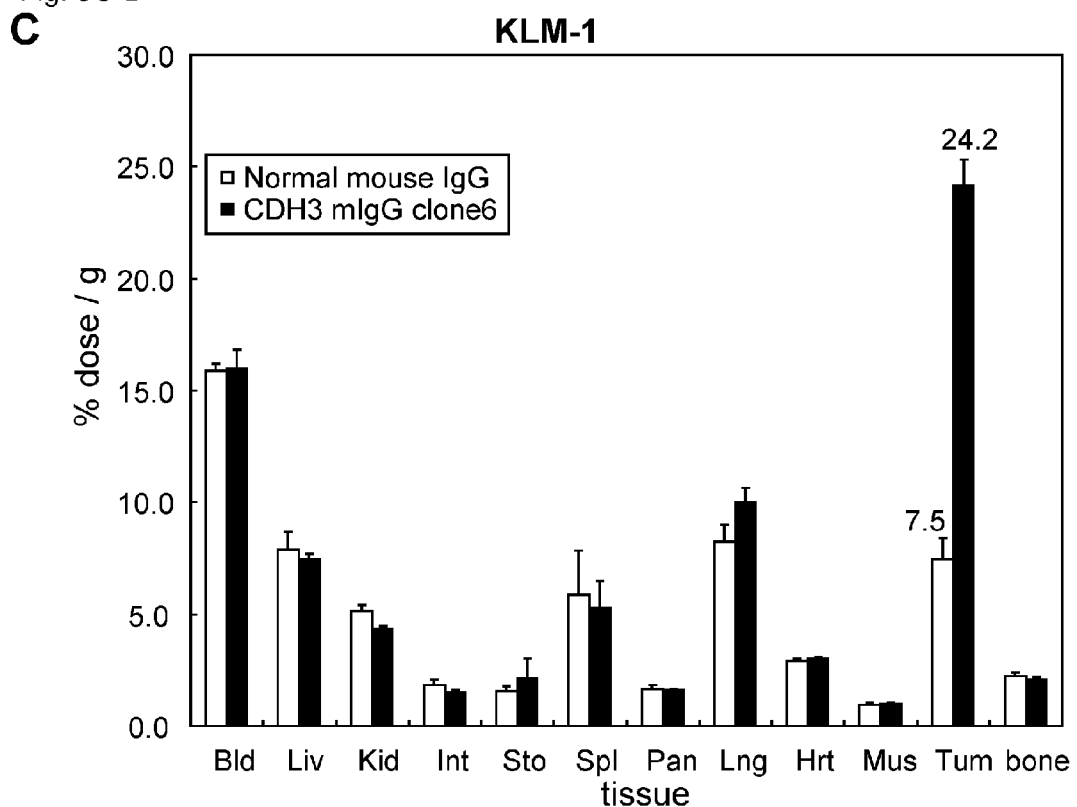
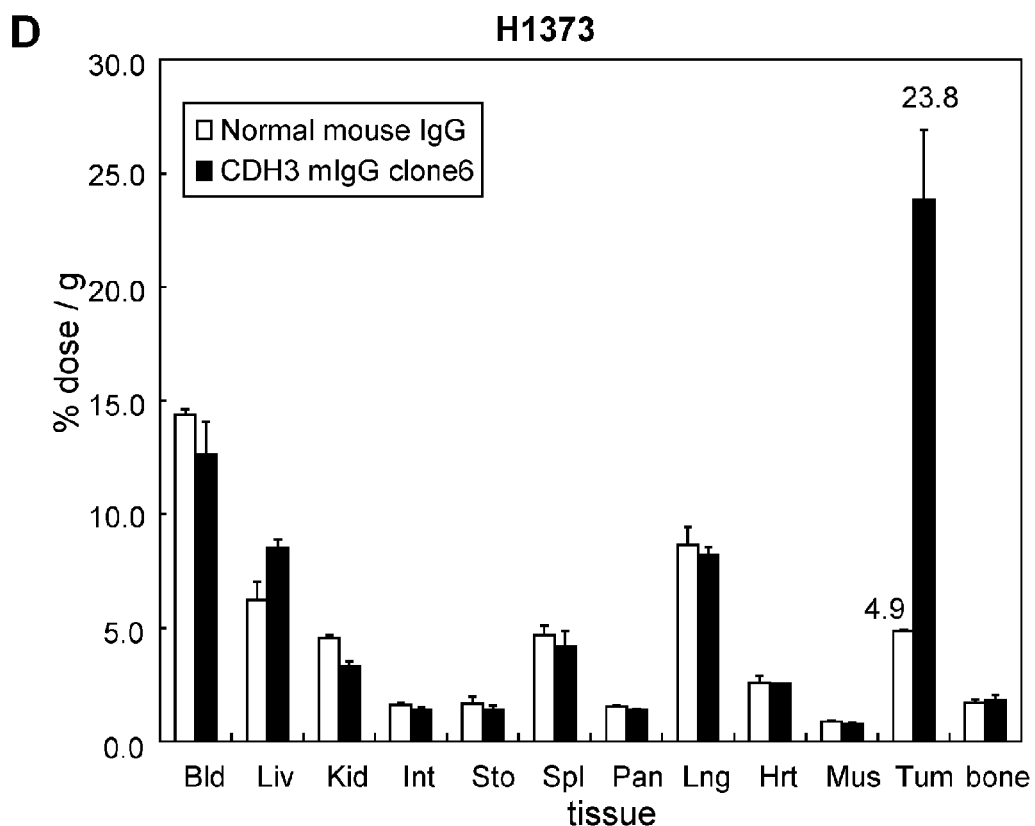

Fig. 4A-B
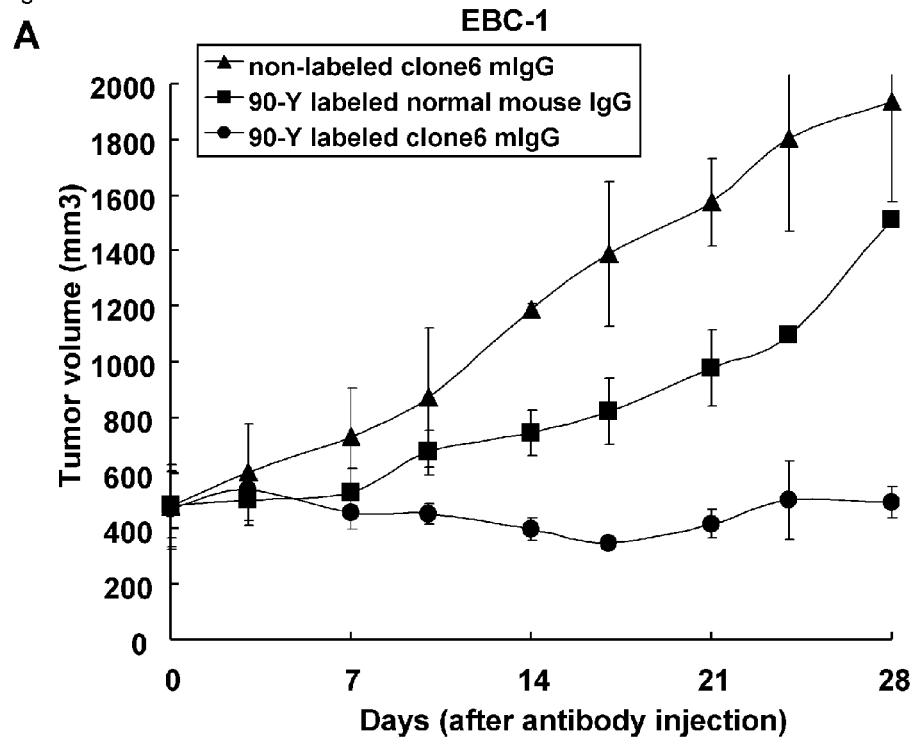
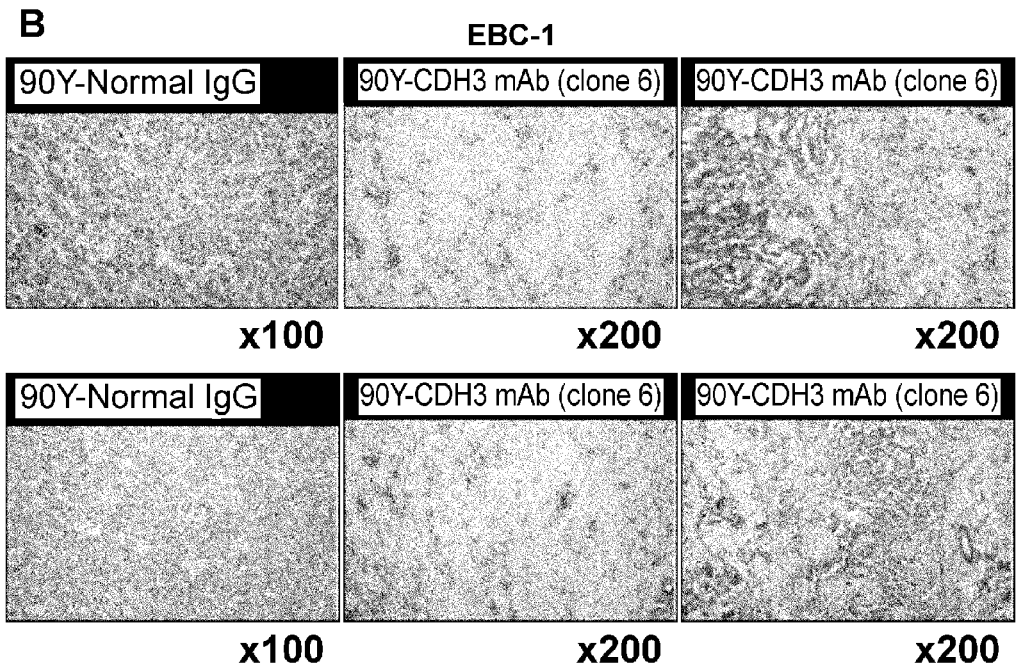

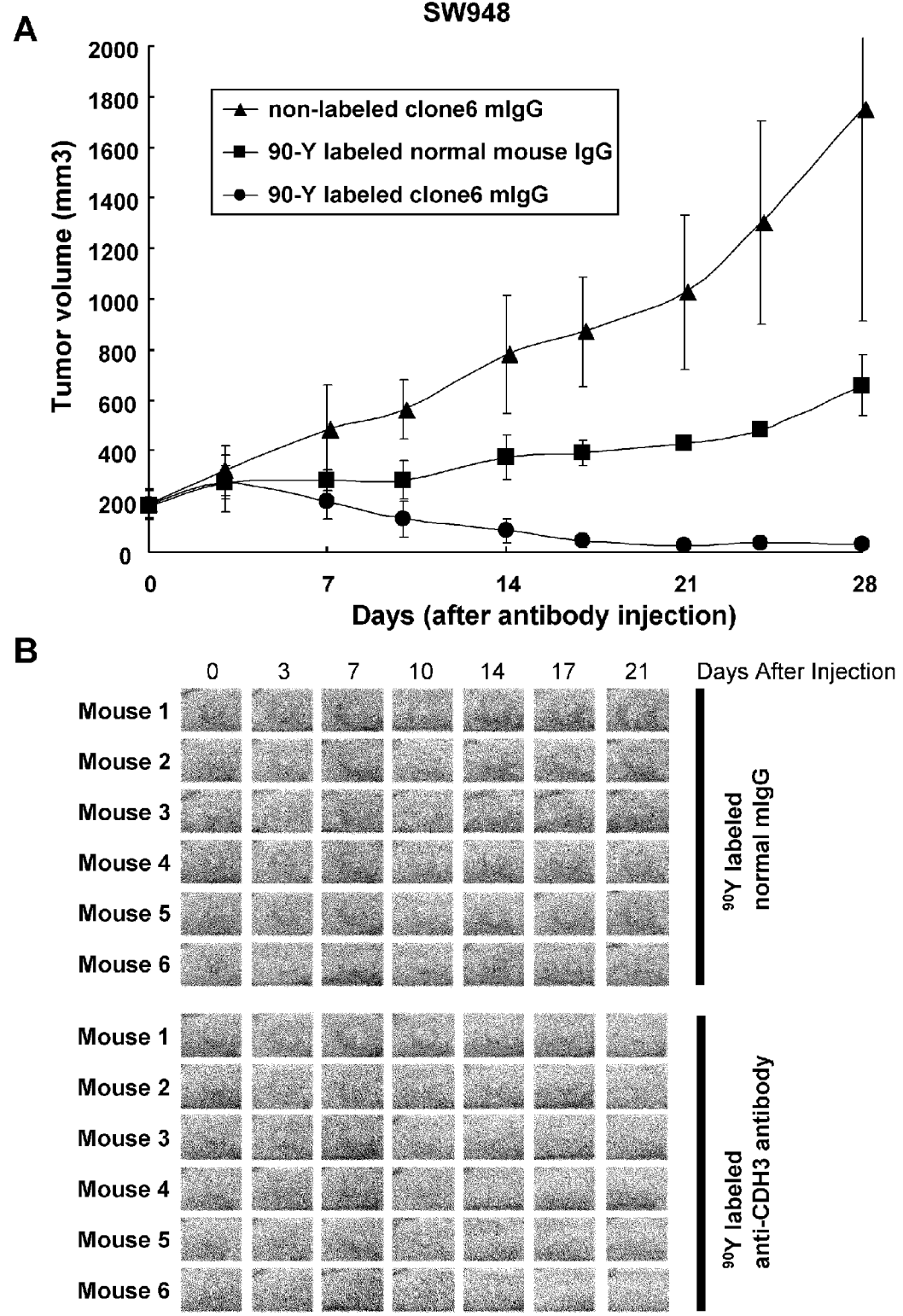
Fig. 5A-B

ANTI-CDH3 ANTIBODIES LABELED WITH RADIOISOTOPE LABEL AND USES THEREOF

CROSS-REFERENCES TO RELATED APPLICATIONS

This application is a U.S. National Stage Application of PCT/JP2009/003009, filed Jun. 30, 2009, which claims the benefit of U.S. Provisional Application Ser. No. 61/076,982, filed Jun. 30, 2008, the contents of which are hereby incorporated by reference in their entirety.

TECHNICAL FIELD

The present invention relates to methods for damaging cancer cells using anti-CDH3 antibodies conjugated with radioisotope label, or to compositions for this purpose.

BACKGROUND ART

Cadherins are cell-cell adhesion glycoproteins that form calcium-dependent intercellular junctions and play an essential role in morphogenesis and in the development and maintenance of adult tissues and organs (Conacci-Sorrell M, et al., J Clin Invest, 109:987-91, (2002)). During embryogenesis, the cell expression of specific cadherins results in homophilic interactions that are critical in the process of cell sorting and tissue stratification (Nose A, et al., Cell, 54:993-1001, (1988), Steinberg M S, et al., Proc Natl Acad Sci USA, 91:206-9, (1994) and Takeichi M. Science, 251:1451-5, (1991)). Alterations in these cellular attachments play an important role in cell destabilization and may modify the carefully regulated differentiation process of the epithelial structures (Daniel C W, et al., Dev Biol, 169:511-9, (1995) and Nose A and Takeichi M. J Cell Biol, 103:2649-58, (1986)). For this reason, the functional loss or overexpression of cadherins and the molecular mechanisms underlying the control of the genes codifying these proteins have been implicated in carcinogenesis (Behrens J. Cancer Metastasis Rev, 18:15-30 (1999)).

The cadherin family is subdivided into various subfamilies, including the classical E-, P-, and N-cadherins, each demonstrating a specific tissue distribution (Takeichi M. Development, 102:639-55 (1988)). Although E-cadherin is expressed in all epithelial tissues, the expression of P-cadherin (CDH3) is only restricted to the basal or lower layers of stratified epithelia, including prostate and skin, and also to the breast myoepithelial cells (Takeichi M. J Cell Biol 103:2649-58, (1986) and Shimoyama Y, et al., Cancer Res, 49:2128-33 (1989)).

A large body of evidence now also reveals that aberrant P-cadherin expression is associated with cell proliferation and with tumors of the colon, breast, lung, thyroid, and cervix (Gamallo, Modern Pathology, 14:650-654, (2001); and Stefansson, et al., J. Clin. Oncol. 22(7):1242-1252 (2004)). Human P-cadherin was reported to be the antigen recognized by the NCC-CAD-299 monoclonal antibody raised against a vulvar epidermoid carcinoma (Shimoyama, et al., Cancer Res., 49:2128-2133 (1989)). Modulation of P-cadherin mediated adhesion and intracellular signaling is expected to result in decreased proliferation and survival of tumor cells in vivo. Accordingly, in view of the pivotal role that P-cadherin appears to possess in cell proliferation and solid tumor progression, it is desirable to generate antibodies to P-cadherin that can provide a therapeutic benefit to patients with a variety of cancers.

Monoclonal antibodies against cancer-specific molecules have been proved to be useful in cancer treatment (Harris, M. (2004). Lancet Oncol, 5, 292-302.). In addition to successful examples of clinical application of the humanized or chimeric antibodies such as trastuzumab (Baselga, J. (2001). Oncology, 61, Suppl 2 14-21.), rituximab (Maloney, D. G., et al. (1997). Blood, 90, 2188-2195.) and bevacizumab (Ferrara, N., et al. (2004). Nat Rev Drug Discov, 3, 391-400.) for breast cancer, malignant lymphoma and colon cancer, a number of monoclonal antibodies against other molecular targets are in development and being evaluated their anti-tumor activities. These monoclonal antibodies are expected to provide a hope to patients having tumors that have no effective treatment. One of the other important issues for these monoclonal antibodies is achievement of selective therapeutic effects to cancer cells without severe toxicity due to their specific reaction to cells expressing target molecules (Crist, W. M., et al. (2001). J Clin Oncol, 19, 3091-3102.; Wunder, J. S., et al. (1998). J Bone Joint Surg Am, 80, 1020-1033.; Ferguson, W. S. and Goorin, A. M. (2001). Cancer Invest, 19, 292-315, WO2002/097395, WO2004/110345, WO2006/114704, WO2007/102525.).

BRIEF SUMMARY OF THE INVENTION

The present invention provides monoclonal antibodies against CDH3, which specifically recognize the polypeptide having the amino acid sequence as shown in SEQ ID NO: 3. In vivo tumor-binding activity of this antibody was demonstrated using a fluorescent in vivo imaging system with near-infrared fluorescence in addition to the conventional method with radionuclides. The present invention provides evidence of significant antitumor effect in xenograft mice bearing several cancer cell lines, wherein the mice are treated with a single or twice administration of 90Y-labeled anti-CDH3 monoclonal antibodies (clone#6) and chimeric thereof (ch-#6).

Specifically, the present invention relates to the following:

[1] An antibody or a fragment thereof, which specifically recognizes a polypeptide having an amino acid sequence as shown in SEQ ID NO: 3. In typical embodiments, the antibody or a fragment of the present invention comprises an H (heavy) chain V (variable) region comprising a complementarity determining region (CDR) having the amino acid sequences shown in SEQ ID NOs: 13, 14 and 15 or a CDR or functionally equivalent thereto (i.e., binds to the same antigenic determinant) and an L (light) chain V region comprising a CDR having the amino acid sequences shown in SEQ ID NOs: 16, 17 and 18 a CDR functionally equivalent thereto (i.e., binds to the same antigenic determinant), and which is capable of specifically binding to a CDH3 protein or a partial peptide thereof. In more typical embodiments, the antibody is selected from the group consisting of a mouse antibody, a chimeric antibody, a humanized antibody, a human antibody, an antibody fragment, and single-chain antibody.

[2] The antibody or fragment thereof of the invention can be labeled with a radioisotope label. In typical embodiments, the radioisotope label is selected from the group consisting of 90yttrium (90Y), 125iodine (125I) and 111 indium (111In).

[3] A composition, for treating or preventing cancer comprising a pharmaceutically effective amount of the antibody or fragment thereof of the invention. In typical embodiments, the cancer is a pancreatic, lung, colon, prostate, breast, gastric or liver cancer.

[4] A method for treating or preventing cancer in a subject, the method comprising administering to said subject a pharmaceutically effective amount of the antibody or fragment thereof of the invention. In typical embodiments, the cancer is a pancreatic, lung, colon, prostate, breast, gastric or liver cancer.

[5] A method for diagnosis or prognosis of a disease that is associated with CDH3 or of a predisposition to develop the disease in a subject, comprising
(a) contacting a sample or a specimen from the subject with the antibody or fragment thereof of the invention;
(b) detecting the presence or absence of the CDH3 protein in the sample or specimen; and
(c) determining whether or not the subject suffers from or is at risk of developing the disease based on the relative abundance of the CDH3 protein compared to a control.

In typical embodiments, the cancer is a pancreatic, lung, colon, prostate, breast, gastric or liver cancer cell.

[6] A kit for diagnosis or prognosis of a disease associated with CDH3, comprising the antibody or fragment of the present invention. In typical embodiments, the cancer is a pancreatic, lung, colon, prostate, breast, gastric or liver cancer.

BRIEF DESCRIPTION OF THE DRAWINGS

FIG. 1 shows the results of CDH3 expression in cell lines. Upper panels show flow cytometory analysis using each antibody. KLM-1 and H358 are CDH3 positive cancer cell lines. MIAPaCa-2 is a negative control cell line. Anti-erbB2 is used as positive control. All of disclosed anti-CDH3 antibody clones can specifically recognize the cells expressing CDH3. Lower panels are photographs depicting the results of Semi-quantitative RT-PCR analysis for the CDH3 gene in cancer cell lines.

FIG. 2A shows in vivo fluorescence imaging of tumor-bearing mice after injection of each Alexa 647-labeled antibody clone. Fluorescence-labeled antibody clones are administered intravenously. All fluorescence images were acquired at 3, 24, 48 and 72 hours after injection. Fluorescence signal from Alexa647 was pseudo-colored which means that red is high density.

FIG. 2B show biodistributions of $^{111}$In-labeled anti-CDH3 antibodies in EBC1 human lung cancer xenografted mice respectively (B: clone1).

FIG. 2C-D show biodistributions of $^{111}$In-labeled anti-CDH3 antibodies in EBC1 human lung cancer xenografted mice respectively (C: clone3, D: clone4).

FIG. 2E-F show biodistributions of $^{111}$In-labeled anti-CDH3 antibodies in EBC1 human lung cancer xenografted mice respectively (E: clone5, F: clone6).

FIG. 3A-B shows biodistribution of $^{111}$In-labeled clone#6 antibody or control antibody. The grafted tumors (A: EBC-1, B: SW948), liver, kidney, intestines, stomach, spleen, pancreas, lung, heart, muscle and bones are isolated at 48 hours after injection, and the radio-activities were measured. Black box shows the anti-CDH3 antibody's accumulation to the each tissue.

FIG. 3C-D shows biodistribution of $^{111}$In-labeled clone#6 antibody or control antibody. The grafted tumors (C: KLM-1, D: H1373), liver, kidney, intestines, stomach, spleen, pancreas, lung, heart, muscle and bones are isolated at 48 hours after injection, and the radio-activities were measured. Black box shows the anti-CDH3 antibody's accumulation to the each tissue.

FIG. 4 shows the effect of $^{90}$Y-labeled anti-CDH3 antibody (clone#6) on tumor growth. FIG. 4A shows that single administration of $^{90}$Y-labeled anti-CDH3 antibody (clone#6) suppresses the growth of EBC-1 cells grafted in nude mice. FIG. 4B shows HE-staining of the tumor tissue after the injection. As shown in the right panels, the tumor tissue substitutes for fiber tissue stained by the eosin (red color).

FIG. 5A shows that single administration of $^{90}$Y-labeled anti-CDH3 antibody (clone#6) suppresses the growth of SW948 cells grafted in nude mice. FIG. 5B shows the photograph of tumors in appearance. After the $^{90}$Y-labeled anti-CDH3 antibody injection, the tumor apparently reduces.

DESCRIPTION OF EMBODIMENTS

Figure 3E:
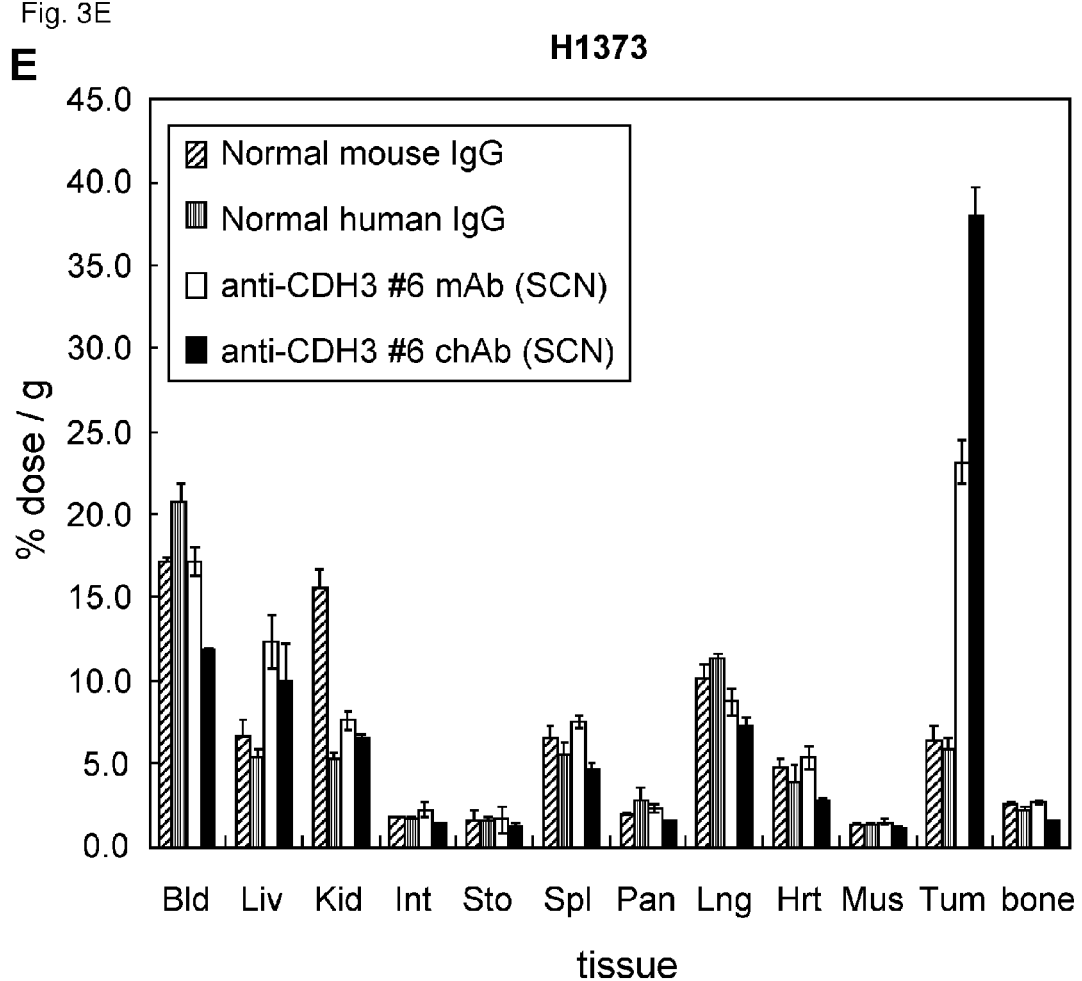
FIG. 3E shows biodistribution of $^{111}$In-labeled anti-CDH3 chimeric or mouse antibodies #6, or normal human IgG or mouse IgG1 as control. The grafted tumors (H1373), liver, kidney, intestines, stomach, spleen, pancreas, lung, heart, muscle and bones are isolated at 48 hours after injection, and the radio-activities were measured. Black box shows the anti-CDH3 chimeric antibody's accumulation to the each tissue. White box shows the anti-CDH3 mouse antibody's accumulation to the each tissue.

The present invention relates to anti-CDH3 antibody and compositions and their use in treating or preventing a cancer. In a typical embodiment, the antibody is labeled with a radioisotope label.

cDNA microarrays for gene expression analysis of pancreatic cancer cells and normal cells collected from pancreatic cancer patients has been reported (Nakamura et al., (2004) Oncogene; 23: 2385-400). A number of genes with specifically enhanced expression in pancreatic cancer cells were subsequently identified. Of these genes with altered expression in pancreatic cancer cells, one gene, placental cadherin (P-cadherin; CDH3) (Genbank Accession No. NM_001793; SEQ ID No. 1, 2) gene encoding cytoplasmic membrane protein with low levels of expression in major organs was selected as a target gene for pancreatic cancer therapies. By selecting genes with low levels of expression in major organs, the danger of side effects is avoided. In addition, a similar over-expression of CDH3 was confirmed in other cancer cell lines, such as the lung, colorectal, prostate, breast, gastric and liver-cancer cell lines (WO/2007/102525).

DEFINITION

The terms "antibody" as used herein is intended to include immunoglobulins and fragments thereof which are specifically reactive to the designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM).

"Antibody fragments" is a portion of an intact antibody, generally comprises the antigen binding or variable region of the intact antibody. Accordingly, in the present invention, antibody fragment may comprise antigen binding portion of the intact antibody. The term "antigen-binding portion" of an antibody (or simply "antibody portion" or "antibody fragment"), as used herein, refers to one or more immunological active fragments of an antibody that retain the ability to specifically bind to an antigen (e.g., CDH3). It has been shown that the antigen-binding function of an antibody can be performed by fragments of a full-length antibody. Examples of antibody fragments include Fab, Fab', F(ab')2, and Fv fragments; linear antibodies; and single chain antibody molecules. Regardless of structure, an antibody fragment binds with the same antigen that is recognized by the intact antibody. The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

One skilled in the art will understand that antibodies comprising variable regions (including complementarity determining regions) substantially corresponding the sequences of the antibodies of the invention can vary from the referred-to sequence and still specifically recognize the same antigenic determinant. This variation from the sequence may be stated in terms of a percentage of identical amino acids within the sequence. In some embodiments, this percentage is from about 90% to about 100%, e.g., 95, 96, 97, 98, 99, or 100%

The terms "identical" or percent "identity," in the context of two or more polypeptide sequences, refer to two or more sequences or subsequences that are the same or have a specified percentage of amino acid residues or nucleotides that are the same (i.e., 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids in length, or more preferably over a region that is 50-100 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information.

Production of Antibodies

The subject invention uses antibodies to CDH3. These antibodies will be provided by known methods.

Exemplary techniques for the production of the antibodies used in accordance with the present invention are described.

(i) Polyclonal Antibodies

Polyclonal antibodies are preferably raised in animals by multiple subcutaneous (sc) or intraperitoneal (ip) injections of the relevant antigen (e.g., SEQ ID NO: 3) and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOC12, or R'N=C=NR, where R' and R are different alkyl groups.

Animals are immunized against the antigen, immunogenic conjugates, or derivatives by combining, e.g. 100 mcg or 5 mcg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent.

Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256: 495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133: 300 1 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5: 256-262 (1993) and Pluckthun, Immunol. Revs., 130: 151-188 (1992).

Another method of generating specific antibodies, or antibody fragments, reactive against a CDH3 is to screen expression libraries encoding immunoglobulin genes, or portions thereof, expressed in bacteria with a CDH3 protein or peptide. For example, complete Fab fragments, VH regions and Fv regions can be expressed in bacteria using phage expression libraries. See for example, Ward et al., Nature 341: 544-546 (1989); Huse et al., Science 246: 1275-1281 (1989); and McCafferty et al., Nature 348: 552-554 (1990). Screening such libraries with, for example, a CDH3 peptide, can identify immunoglobulin fragments reactive with CDH3. Alternatively, the SCID-hu mouse (available from Genpharm) can be used to produce antibodies or fragments thereof.

In a further embodiment, antibodies or antibody fragments can be isolated from antibody phage libraries generated using the techniques described in McCafferty et al., Nature, 348: 552-554 (1990). Clackson et al., Nature, 352: 624-628 (1991) and Marks et al., J. MoL BioL, 222: 581-597 (1991) describe the isolation of murine and human antibodies, respectively, using phage libraries. Subsequent publications describe the production of high affinity (nM range) human antibodies by chain shuffling (Marks et al., BioTechnology, 10: 779-783 (1992)), as well as combinatorial infection and in vivo recombination as a strategy for constructing very large phage libraries (Waterhouse et al., Nuc. Acids. Res., 21: 2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. ScL USA, 81: 6851 (1984)), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Any antibodies that bind to extracellular domain of CDH3 protein having the amino acid sequence of SEQ ID NO: 3 can be used for the present invention. Accordingly, as long as antibodies recognize SEQ ID NO: 3, such antibodies may be used for a method, or composition of the present invention. In preferred embodiments, antibodies recognizing the amino acid sequence of SEQ ID NO: 3 may bind to cells expressing CDH3 comprising at least transmembrane and extracellular domains thereof.

Meanwhile, the present invention also provides an antibody suitable for treating or diagnosing CDH3 associated disease. In particular, the antibody defined with following properties is preferable for such use in purpose.

VH and VL domains of antibodies of the present invention each include three CDRs designated as CDR1, CDR2, and CDR3, separated by framework regions. Amino acid sequences of the CDRs are not particularly limited so long as the antibody can specifically bind to CDH3. Examples of preferred CDR amino acid sequences include, but are not limited to:

| | | |
|---|---|---|
| VH CDR1: | SYWIH, | (SEQ ID NO: 13) |
| VH CDR2: | EIDPSDNYTYYNQNFKG, | (SEQ ID NO: 14) |
| VH CDR3: | SGYGNLFVY, | (SEQ ID NO: 15) |
| VL CDR1: | SATSSVTYMY, | (SEQ ID NO: 16) |
| VL CDR2: and | RTSNLAS, | (SEQ ID NO: 17) |
| VL CDR3: | QHYHIYPRT | (SEQ ID NO: 18) |

One of the predictive methods of CDRs is described in Kabat E. A. et al. (1991) Sequence of Proteins of Immunological Interest. 5th Edition. NIH Publication No. 91-3242.

In a more preferred embodiment, VH corresponds to the amino acid sequence of SEQ ID NO: 11, and VL corresponds to the amino acid sequence of SEQ ID NO: 12.

In accordance with the present invention, the monoclonal antibodies and binding fragments thereof may be characterized as:
i) antibody comprising variable regions defined by the amino acid sequences of SEQ ID NOs: 11 and 12;
ii) antibodies that are capable of binding to the same antigenic determinant as does the monoclonal antibody defined by the amino acid sequences of the CDRs described here;
iii) binding fragments of the monoclonal antibodies defined by the amino acid sequences; or
iv) binding fragments of a monoclonal antibody capable of binding to the same antigenic determinant as does the monoclonal antibody defined by the amino acid sequences.

The standard techniques of molecular biology may be used to prepare DNA sequences coding for the chimeric and CDR-grafted products. Genes encoding the CDR of an antibody of interest can be prepared, for example, by using the polymerase chain reaction (PCR) to synthesize the variable region from RNA of antibody-producing cells (see, for example, Larrick et al., "Methods: a Companion to Methods in Enzymology", vol. 2: page 106 (1991); Courtenay-Luck, "Genetic Manipulation of Monoclonal Antibodies" in Monoclonal Antibodies: Production, Engineering and Clinical Application; Ritter et al. (eds.), page 166 (Cambridge University Press, 1995), and Ward et al., "Genetic Manipulation and Expression of Antibodies" in Monoclonal Antibodies: Principles and Applications; Birch et al. (eds.), page 137 (Wiley-Liss, Inc., 1995)). DNA sequences coding for the chimeric and CDR-grafted products may be synthesised completely or in part using oligonucleotide synthesis techniques. Site-directed mutagenesis and polymerase chain reaction techniques may be used as appropriate. For example, oligonucleotide directed synthesis as described by Jones et al., (1986) Nature.; 321:522-5 may be used. Also oligonucleotide directed mutagenesis of a pre-existing variable region as, for example, described by Verhoeyen et al., (1988) Science.; 239:1534-6 or Riechmann et al., (supra) may be used. Also enzymatic filling in of gapped oligonucleotides using T4 DNA polymerase as, for example, described by Queen et al., (1989) Proc Natl Acad Sci USA.; 86:10029-33; PCT Publication WO 90/07861 may be used.

Any suitable host cell/vector system may be used for expression of the DNA sequences coding for the CDR-grafted heavy and light chains. Bacterial, e.g., E. coli, and other microbial systems may be used, in particular for expression of antibody fragments such as FAb and (Fab')₂ fragments, and especially Fv fragments and single-chain antibody fragments, e.g., single-chain Fvs. Eucaryotic, e.g., mammalian, host cell expression systems may be used, in particular, for production of larger CDR-grafted antibody products, including complete antibody molecules. Suitable mammalian host cells include CHO cells and myeloma or hybridoma cell lines.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321: 522-525 (1986); Reichmann et al., Nature, 332: 323-327 (1988); Verhoeyen et al., Science, 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so called "best-fit" method, the sequence of the variable domain of a rodent antibody is screened against the entire library of known human variable-domain sequences. The human sequence which is closest to that of the rodent is then accepted as the human framework region (FR) for the humanized antibody (Suns et al., J. Immunol., 151: 2296 (1993); Chothia et al., J. Mol. Biol, 196: 901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89: 4285 (1992); Presta et al., J. Immunol., 151: 2623 (1993)).

It is further important that antibodies are humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen, is achieved. In general, the hypervariable region residues are directly and most substantially involved in influencing antigen binding.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ line mutant mice will result in the production of human antibodies upon antigen challenge. See, e.g., Jakobovits et al., Proc. Mad. Acad. Sci. USA, 90: 255 1 (1993); Jakobovits et al., Nature, 362: 255-258 (1993); Bruggermann et al., Year in immuno., 7: 33 (1993); and U.S. Pat. Nos. 5,591,669, 5,589, 369 and 5,545,807.

Alternatively, phage display technology (McCafferty et al., Nature 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3: 564-571 (1993). Several sources of V-gene segments can be used for phage display.

Clackson et al., Nature, 352: 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self antigens) can be isolated essentially following the techniques described by Marks et al., J. Mol. Biol, 222: 581-597 (1991), or Griffith et al., EMBO J. 12: 725-734 (1993). See, also, U.S. Pat. Nos. 5,565,332 and 5,573,905.

Human antibodies may also be generated by in vitro activated B cells (see U.S. Pat. Nos. 5,567,610 and 5,229,275). A preferred means of generating human antibodies using SCID mice is disclosed in commonly-owned, co-pending applications.

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24: 107-117 (1992) and Brennan et al., Science, 229: 81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10: 163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870. Such linear antibody fragments may be monospecific or bispecific.

(vi) Bispecific Antibodies

Bispecific antibodies are antibodies that have binding specificities for at least two different epitopes. Exemplary, an anti-cancer cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIH(CD 16) so as to focus cellular defense mechanisms to the cancer cell. Bispecific antibodies may also be used to localize cytotoxic agents to the cancer cell. These antibodies possess a cancer cell marker-binding arm and an arm which binds the cytotoxic agent (e.g. saporin, anti-interferon-a, vinca alkaloid, ricin A chain, methotrexate or radioactive isotope hapten). Bispecific antibodies can be prepared as full length antibodies or antibody fragments (e.g. $F(ab)_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305: 537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10: 3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CHI) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121: 210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chains) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers (Kostelny et al., J Immunol. 148 (5): 1547-1553 (1992)). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90: 6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J Immunol., 152: 5368 (1994).

Antibodies with more than two valencies are contemplated. For example, trispecific antibodies can be prepared. Tutt et al. J; Immunol. 147: 60 (1991).

Antibody Conjugates and Other Modifications

The antibodies used in the methods or included in the articles of manufacture herein are optionally conjugated to a cytotoxic or therapeutic agent.

As used herein a therapeutic agent includes any chemotherapeutic agent which is useful in the treatment of cancer. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylmelamines including altretamine, triethylenemelamine, trietylenephosphoramide, triethylenethiophosphaoramide and trimethylolmelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromoinycins, dactinomycin, daunorubicin, detorubicin, 6-diazo-5-oxo-L-norleucine, doxorubicin, epirubicin, esorubicin, idambicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; efornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK@ razoxane; sizofurane; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C");

cyclophosphamide; thiotepa; taxoids, e.g. paclitaxel (TAXOLO, Bristol-Myers Squibb Oncology, Princeton, N.J.) and doxetaxel (TAXOTEW, Rh6ne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this therapeutic agent are anti-hormonal agents that act to regulate or inhibit hormone action on tumors such as anti-estrogens including for example tamoxifen, raloxifene, aromatase inhibiting 4 (5)-imidazoles, 4-hydroxytamoxifen, trioxifene, keoxifene, onapristone, and toremifene (Fareston); and anti-androgens such as flutamide, nilutamide, bicalutamide, leuprolide, and goserelin; and pharmaceutically acceptable salts, acids or derivatives of any of the above.

Conjugates of an antibody and one or more small molecule toxins, such as a calicheamicin, a maytansine (U.S. Pat. No. 5,208,020), a trichothecene, and CC 1065 are also contemplated herein. In one preferred embodiment of the invention, the antibodies are conjugated to one or more maytansine molecules (e.g. about 1 to about 10 maytansine molecules per antibodies molecule). Maytansine may, for example, be converted to May SS-Me which may be reduced to May-$SH_3$ and reacted with modified antibodies (Chari et al. Cancer Research 52: 127-131 (1992)) to generate a maytansinoid-antibody conjugate.

Alternatively, the antibody may be conjugated to one or more calicheamicin molecules. The calicheamicin family of antibiotics is capable of producing double stranded DNA breaks at sub-picomolar concentrations. Structural analogues of calicheamicin which may be used include, but are not limited to gamma1I, alpha2I, alpha3I, N-acetyl-gammaII, PSAG and OI1 (Hinman et al. Cancer Research 53: 3336-3342 (1993) and Lode et al, Cancer Research 58: 2925-2928 (1998)).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the trichothecenes. See, for example, WO 93/21232 published Oct. 28, 1993.

The present invention further contemplates antibody conjugated with a variety of radioactive isotopes. Examples include $^{111}$In, $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu. In the present invention, antibody of the present invention may be labeled with radio-nuclides just prior to use, or provided as radiolabeled antibody. The skilled practitioner will realize that there are numerous radionuclides and chemocytotoxic agents that can be coupled to tumor-specific antibodies by well-known techniques and delivered to a site to specifically damaging tumor cells and tissue. (See, for example, U.S. Pat. No. 4,542,225 to W. A. Blattler et al., issued Sep. 17, 1985; and Pastan et al., 1986, Cell, 47:641-648). For example, imaging and cytotoxic reagents that are suitable for use include $^{125}$I, $^{123}$I, $^{111}$In (e.g., Sumerdon et al., 1990, Nucl. Med. Biol., 17:247-254), and $^{99m}$Tc; fluorescent labels such as fluorescein and rhodamine; chemiluminescent labels such as luciferin, and paramagnetic ions for use in magnetic resonance imaging (Lauffer et al., 1991, Magnetic Resonance in Medicine, 22:339-342). Antibodies can be labeled with such reagents using protocols and techniques known and practiced in the art. See, for example, Wenzel and Meares, Radioimmunoimaging and Radioimmunotherapy, Elsevier, N.Y., 1983; Colcer et al., 1986, Meth. Enzymol., 121:802-816; and Monoclonal Antibodies for Cancer Detection and Therapy, Eds. Baldwin et al., Academic Press, 1985, pp. 303-316, for techniques relating to the radiolabeling of antibodies. Yttrium-90 ($^{90}$Y) labeled monoclonal antibodies have been described for maximizing the dose delivered to the tumor or cancer cells and/or tissue, while limiting toxicity to normal tissues (e.g., Goodwin and Meares, 1997, Cancer Supplement, 80:2675-2680). Other cytotoxic radionuclides including, but not limited to, Iodine-131 ($^{131}$I) and Rhenium-186 can also be used for labeling monoclonal antibodies of the present invention. Among the radionuclides, Yttrium-90 ($^{90}$Y) may be suitable for radioimmunotherapy, since Yttrium-90 ($^{90}$Y) provides advantages over Iodine-131 ($^{131}$I) because it delivers higher beta energy (2.3 MeV vs 0.61 MeV) to the tumor and has path length of 5 to 10 mm resulting in the improved ability to kill both targeted and neighboring cells, an advantage particularly in bulky or poorly vascularized tumor.

The detectable/detecting label used is selected according to the imaging modality to be used. For example, radioactive labels, such as Indium-111 ($^{111}$In), Technetium-99m ($^{99m}$Tc), or Iodine 131 ($^{131}$I), can be used for planar scans or for single photon emission computed tomography (SPECT). Also, positron-emitting labels such as Fluorine-19 can be used in positron emission tomography (PET). Paramagnetic ions, such as Gadlinium(III) or Manganese(II) can be used in magnetic resonance imaging (MRI). The monoclonal antibodies can also be labeled with radio-opaque labels for the visualization of cancer cells after injection, for example, by X-ray, CATscan, or MRI. In particular, for CDH3 relating disease (e.g. cancers), localization of the label within the cancers permits the determination of the spread of the disease. The amount of label that is present and detectable within the cancers expressing CDH3, for example, allows the determination of the presence or absence of cancer or tumor in the subject to be diagnosed.

Conjugates of the antibody and cytotoxic agent may be made using a variety of bifunctional protein coupling agents such as N-succinimidyl-3-(2-pyriylditliol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody (See WO94/11026). The linker may be a "cleavable linker" facilitating release of the cytotoxic drug in the cell. For example, an acid-labile linker, peptidase-sensitive linker, dimethyl linker or disulfide-containing linker (Charm et al. Cancer Research 52: 127-131 (1992)) may be used.

Alternatively, a fusion protein comprising the antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

The antibodies of the present invention may also be conjugated with a prodrug activating enzyme which converts a prodrug (e.g. a peptidyl chemotherapeutic agent, see WO81/01145) to an active anti-cancer drug (See, for example, WO 88/07378 and U.S. Pat. No. 4,975,278).

The enzyme component of such conjugates includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic5-fluorocytosine into the anti-cancer drug, fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydratecleaving enzymes such as 13-galactosidase and neuraminidase useful for converting glycosylated prodrugs into free drugs; 13-lactamase useful for converting drugs derivatized with 13-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population.

The enzymes of this invention can be covalently bound to the antibody by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984)).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol.

The antibodies disclosed herein may also be formulated as liposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. J; Biol. Chem. 257: 286-288 (1982) via a disulfide interchange reaction. A chemotherapeutic agent is optionally contained within the liposome (See Gabizon et al. A National Cancer Inst. 81 (19) 1484 (1989)).

Amino acid sequence modifications of antibodies described herein are contemplated. For example, it may be desirable to improve the binding affinity and/or other biological properties of the antibody. Amino acid sequence variants of the antibody are prepared by introducing appropriate nucleotide changes into the antibody encoding nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells Science, 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of an enzyme, or a polypeptide which increases the serum half-life of the antibody.

Another type of variant is an amino acid substitution variant. These variants have at least one amino acid residue in the antibody molecule replaced by different residue. The sites of greatest interest for substitutional mutagenesis of antibody include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Naturally occurring residues are divided into groups based on common side-chain properties:
(1) hydrophobic: norleucine, met, ala, val, leu, ile;
(2) neutral hydrophiuic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bonds may be added to the antibody to improve its stability (particularly where the antibody is a fragment such as an Fv fragment).

A particularly preferred type of substitutional variant involves substituting one or more hypervariable region residues of a parent antibody (e.g. a humanized or human antibody). Generally, the resulting variants selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain.

Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly seine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more seine or threonine residues to the sequence of the original antibody (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibodies used in the invention to improve effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J limmunol 148: 2918-2922 (1992).

Homodimeric antibodies with enhanced anti-tumor activity may also be prepared using heterobifunctional cross-linkers as described in Wolff et al. Cancer Research 53: 2560-2565 (1993). Alternatively, an antibody can be engineered which has dual Fc regions and may thereby have enhanced complement lysis and ADCC capabilities (See Stevenson et al. Anti-Cancer Drug Design 3: 219-230 (1989)).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Diagnosing a Disease that is Associated with CDH3 or of a Predisposition to Develop the Disease An anti-CDH3 antibody of the present invention may be used as a marker for diagnosing a disease that is associated with CDH3.

More specifically, by detecting the CDH3 protein with an anti-CDH3 antibody of the present invention in a sample, a disease that is associated with CDH3 can be diagnosed. Thus, the present invention provides methods for diagnosing a disease that is associated with CDH3 or a predisposition for developing a disease that is associated with CDH3 in a subject by detecting the CDH3 protein with an anti-CDH3 antibody of the present invention in the subject. The methods comprise the steps of:

(a) contacting a sample or a specimen from the subject with the antibody or fragment of the present invention;
(b) detecting the CDH3 protein in the sample or specimen; and
(c) judging whether or not the subject suffers from or is at risk of developing the disease based on the relative abundance of the CDH3 protein compared to a control.

In a typical embodiment, a disease that is associated with CDH3 is pancreatic, lung, colon, prostate, breast, gastric or liver cancer.

Alternatively, in a other embodiments, the anti-CDH3 antibody of the present invention may be used for detecting or imaging a cancer in a living body. More specifically, the present invention provides methods of detecting or imaging a cancer which comprise the steps of:
(1) administering to a subject an anti-CDH3 antibody or binding fragment thereof;
(2) detecting accumulation or localization of the antibody in a living body, and
(3) determining the location of the antibody or binding fragment thereof, within the patient Alternatively, according to the present invention, cancer cells or tissues may be detected in a patient. For example, the present invention provides methods for detecting a cancer, in which CDH3 is expressed in tumor tissue in a patient, comprising: administering an antibody or antibody fragment to the subject allowing the antibody or antibody fragment specifically binds to CDH3 in the cells or tissue; visualizing the antibody bound in the cells or tissue; and comparing levels of antibody bound in the cells or tissue to a normal control cells or tissue, wherein an increase in the level of antibody bound to the patient cells or tissue relative to the normal control cells or tissue is indicative of a cancer in the patient.

Preferably, in order to trace the antibody administered into a living body, the antibody may be labeled with detectable molecules. For example, the behavior of antibodies labeled with a fluorescent substance, luminescent substance, or radioisotope can be traced in vivo. Methods for labeling an antibody with such molecules are well known in the art.

Antibodies labeled with a fluorescent substance or a luminescent substance can be observed, for example, using an endoscope or a laparoscope. When using a radioisotope, the localization of an antibody can be imaged by tracing the radioactivity of the radioisotope. In the present invention, the localization of an anti-CDH3 antibody in vivo demonstrates the presence of cancer cells.

Alternatively, an anti-CDH3 antibody of the present invention may be used for in vivo imaging. Specifically, an anti-CDH3 antibody of the present invention labeled for detection may be used in order to visualize CDH3 protein in a living body. For example, the behavior of antibodies labeled with a fluorescent substance, luminescent substance, or radioisotope can be traced in vivo. Antibodies labeled with a fluorescent substance or a luminescent substance can be observed using bioimaging system. When using a radioisotope, the localization of an antibody can be imaged by immunoscintigraphy.

Another embodiment of the present invention provides diagnostics, diagnostic methods and imaging methods for cancers and tumors expressing CDH3 using the monoclonal antibodies or binding fragments of the present invention. The diagnostic uses of the antibody of the present invention embrace primary tumors and cancers, as well as metastases. In preferred embodiments, cancers expressing CDH3 may be selected from the group consisting of pancreatic, lung, colon, prostate, breast, gastric or liver cancers.

A diagnostic method according to the invention comprises administering, introducing, or infusing the monoclonal antibody or their binding fragments as described herein, with or without conjugation to a detectable moiety, such as a radioisotope. Upon administration or infusion, the antibody or binding fragment binds to the tumor or cancer cells, after which the location of the bound antibodies or fragments is detected. For detectably labeled antibodies or fragments, for example, those labeled with a radioisotope, imaging instrumentation may be used to identify the location of the agent within the body. For unlabeled antibodies or fragments, a second detectable reagent may be administered, which locates the bound antibodies or fragments so that they can be suitable detected. Similar methods have been employed for other antibodies, and the skilled practitioner will be aware of the various methods suitable for imaging the location of detectably bound antibody or fragments within the body. As a nonlimiting guide, about 10-1000 microgram (mcg.), preferably about 50-500 mcg, more preferably about 100-300 mcg, more preferably about 200-300 mcg of purified antibody are administered. For example, applicable doses for humans include about 100-200 mcg/kg body weight, or 350-700 mg/m2 of body-surface area.

According to the present invention, an intermediate result for examining the condition of a subject may be provided. Such intermediate result may be combined with additional information to assist a doctor, nurse, or other practitioner to determine that a subject suffers from a disease that is associated with CDH3. Alternatively, the present invention may be used to detect cancerous cells in a subject-derived tissue, and provide a doctor with useful information to determine that the subject suffers from pancreatic, lung, colon, prostate, breast, gastric or liver cancers.

Monitoring and Prognosing a Disease that is Associated with CDH3

Assessing the Efficacy of Treatment:

The differentially expressed CDH3 gene also allows for the course of treatments for a disease that is associated with CDH3 e.g., pancreatic cancer cells (PaC cells), lung cancer cells (LuC cells), colon cancer cells (CC cells), prostate cancer cells (e.g., PrC cells), breast cancer cells (BC cells), gastric cancer cells (GC cells), or liver cancer cells (LiC cells) to be monitored and assessed. Alternatively, according to the present invention, an intermediate result for monitoring the course of treatment of PaC, LuC, CC, PrC, BC, GC, or LiC may be provided. Such intermediate results may be combined with additional information to assist a doctor, nurse, or other practitioner to determine that a subject suffers from pancreatic, lung, colon, prostate, breast, gastric or liver cancers. Thus, CDH3 gene or protein encoded thereby is useful prognostic marker for monitoring clinical outcome of PaC, LuC, CC, PrC, BC, GC, or LiC. Alternatively, the present invention may be used to detect cancerous cells in a subject-derived tissue, and provide a doctor with useful information to assess the course of treatment of PaC, LuC, CC, PrC, BC, GC, or LiC. In this method, a test cell population is provided from a subject undergoing treatment for PaC, LuC, CC, PrC, BC, GC, or LiC. If desired, test cell populations are obtained from the subject at various time points, before, during, and/or after treatment. Expression of the CDH3 gene in the test cell population is then determined and compared to expression of the same genes in a reference cell population which includes cells whose PaC, LuC, CC, PrC, BC, GC, or LiC state is known. In the context of the present invention, the reference cells should not have been exposed to the treatment of interest.

In the context of monitoring and assessing a particular course of treatment for PaC, LuC, CC, PrC, BC, GC, or LiC, the biological sample should be derived from a subject undergoing treatment for pancreatic, lung, colon, prostate, breast, gastric or liver cancers. Preferably, multiple test biological samples are obtained from the subject at various time points before, during or after the treatment.

If the reference cell population contains non-PaC cells, non-LuC cells, non-CC cells, non-PrC cells, non-BC cells, non-GC cells, or non-LiC cells, a similarity in the expression of the CDH3 gene in the test cell population and the reference cell population indicates that the treatment of interest is efficacious. However, a difference in the expression of the CDH3 gene in the test cell population and a normal control reference cell population indicates a less favorable clinical outcome or prognosis. Similarly, if the reference cell population contains PaC cells, LuC cells, CC cells, PrC cells, BC cells, GC cells, or LiC cells, a difference between the expression of the CDH3 gene in the test cell population and the reference cell population indicates that the treatment of interest is efficacious, while a similarity in the expression of the CDH3 gene in the test population and an PaC, LuC, CC, PrC, BC, GC, or LiC control reference cell population indicates a less favorable clinical outcome or prognosis.

Additionally, the expression level of the CDH3 gene determined in a biological sample from a subject obtained after treatment (i.e., post-treatment levels) can be compared to the expression level of the CDH3 gene determined in a biological sample from a subject obtained prior to treatment onset (i.e., pre-treatment levels). A decrease in the expression level in a post-treatment sample indicates that the treatment of interest is efficacious while an increase or maintenance in the expression level in the post-treatment sample indicates a less favorable clinical outcome or prognosis.

As used herein, the term "efficacious" indicates that the treatment leads to a reduction in the expression of CDH3 gene or a decrease in size, prevalence, or metastatic potential of PaC, LuC, CC, PrC, BC, GC, or LiC in a subject. When a treatment of interest is applied prophylactically, the term "efficacious" means that the treatment retards or prevents a lung cancer and/or an esophageal tumor from forming or retards, prevents, or alleviates a symptom of clinical PaC, LuC, CC, PrC, BC, GC, or LiC. Assessment of pancreatic, lung, colon, prostate, breast, gastric or liver tumors can be made using standard clinical protocols.

In addition, efficaciousness can be determined in association with any known method for diagnosing or treating PaC, LuC, CC, PrC, BC, GC, or LiC. PaC, LuC, CC, PrC, BC, GC, or LiC can be diagnosed, for example, histopathologically or alternatively by identifying symptomatic anomalies, e.g., weight loss, loss of appetite, abdominal pain, back pain, anorexia, nausea, vomiting and generalized malaise, weakness, and jaundice.

Assessing the Prognosis of a Subject with a Disease that is Associated with CDH3:

The present invention also provides methods for assessing the prognosis of a subject with a disease that is associated with CDH3, e.g., PaC, LuC, CC, PrC, BC, GC, or LiC, such methods including the step of comparing the expression of the CDH3 gene in a test cell population to the expression of the CDH3 gene in a reference cell population from patients over a spectrum of disease stages. By comparing the gene expression of the CDH3 gene in the test cell population and the reference cell population(s), or by comparing the pattern of gene expression over time in test cell populations from the subject, the prognosis of the subject can be assessed.

Alternatively, according to the present invention, an intermediate result for assessing the prognosis of a subject with PaC, LuC, CC, PrC, BC, GC, or LiC may be provided. Such intermediate result may be combined with additional information to assist a doctor, nurse, or other practitioner to determine that a subject suffers from lung cancer or esophageal cancer. Alternatively, the present invention may be used to detect cancerous cells in a subject-derived tissue, and provide a doctor with useful information to assess the prognosis of a subject with PaC, LuC, CC, PrC, BC, GC, or LiC.

For example, an increase in the expression of the CDH3 gene in a test sample as compared to a normal control sample indicates a less favorable prognosis. Conversely, a similarity in the expression of the CDH3 gene, in a test sample as compared to normal control sample, indicates a more favorable prognosis for the subject.

Kits and Reagents for Diagnosis, Prognosis, or Treatment of a Disease Associated with CDH3:

The present invention provides a kit for diagnosis or prognosis of a disease associated with CDH3. Specifically, the kit includes a reagent for detecting the CDH3 protein. Suitable reagents for detecting the CDH3 protein include an antibody to the CDH3 protein. Preferably, in order to trace the antibody administered into a living body, the antibody may be labeled with detectable molecules. For example, the antibody may be labeled with fluorescent substance, luminescent substance, or radioisotope. Methods for labeling antibodies and detecting the labeled antibodies are well known in the art and any labels and methods may be employed for the present invention.

Furthermore, the kit may include positive and negative control reagents, and a secondary antibody for detecting an antibody against the CDH3 protein. For example, tissue samples obtained from subjects with good prognosis or poor prognosis may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

In other embodiments, the present invention further provides a kit for use in detecting, imaging or treating a cancer within a subject to be diagnosed comprising the antibody against the CDH3 protein. In preferable embodiments, the antibody of the present invention may be labeled with a radioisotope. For example, the kit of the present invention may contain an antibody recognizing CDH3 modified with chelating agent and radioactive substance. MX-DOPA is preferable chelating agent for modifying the antibody. Meanwhile, indium-111 ($^{111}$In) can be used as a tracer for bioimaging. Alternatively, in order for radioimmunotherapy of a cancer expressing CDH3, antibody may be labeled with beta nuclides e.g. Yttrium-90 ($^{90}$Y). In the present invention, indium-111 ($^{111}$In) or Yttrium-90 ($^{90}$Y) may also be provided as salt or solution thereof. Suitable salt of indium-111 ($^{111}$In) or Yttrium-90 ($^{90}$Y) is chloride.

In a preferable embodiment, a disease associated with CDH3 is pancreatic, lung, colon, prostate, breast, gastric or liver cancers.

Therapeutic Uses

Described below are methods and pharmaceutical compositions for treating and/or preventing cancer using the antibody of the present invention. The cancer includes but is not limited to a pancreatic, lung, colon, prostate, breast, gastric or liver cancer cell.

Specifically, the method for treating and/or preventing the cancer in a subject according to the present invention comprises administering to a subject in need thereof the antibody or the fragment described above.

The term "subject" herein refers to a subject who has suffered from the cancer including but is not limited to a pancreatic, lung, colon, prostate, breast, gastric or liver cancer cell. The subject in the present invention may be animals including mammals and avian animals. For example, mammals may include humans, mice, rats, monkeys, rabbits, and dogs.

The antibody or fragment thereof described herein can specifically bind to CDH3 protein, so when the antibody or fragment thereof is administered to a subject, it binds to CDH3 protein in the subject and the growth of the cells expressing CDH3 may be suppressed. Alternatively, when the antibody or fragment thereof may be conjugated with a therapeutic moiety and administered to a subject, it is delivered to a region that expresses CDH3 protein (i.e. suffered region) in a subject and the therapeutic moiety can be selectively delivered to the suffered region and acted thereon. Such therapeutic moiety may be any therapeutics that are known or will be developed for having a therapeutic efficacy on the cancer and includes, but not limited to, a radioisotope label and chemotherapeutic agent. A radioisotope label which can be used as therapeutics can be selected depending on a variety of elements including beta-ray energy and its emission efficiency, the presence or absence of gamma-ray emitted, its energy and emission efficiency, physical half-life, and labeling procedure. Generally, the radioisotope label based on yttrium (such as $^{90}Y$) and iodine (such as $^{125}I$ and $^{131}I$) may be used. A chemotherapeutic agent may be any agent that is known or will be developed for treating the cancer and includes, but not limited to, methotrexate, taxol, mercaptopurine, thioguanine, cisplatin, carboplatin, mitomycin, bleomycin, doxorubicin, idarubicin, daunorubicin, dactinomycin, vinblastine, vincristine, vinorelbine, paclitaxel, and docetaxel. The antibody or fragment thereof described herein can selectively bind to CDH3 protein and not bind to a normal cell, so side effect which is caused by the antibody or fragment thereof, or radioisotope or chemotherapeutic agent can be effectively avoided and therefore the therapeutic potency may be high.

The antibody or fragment thereof described herein can be administered to a subject at effective doses to treat or prevent the CDH3-associated disease. An effective dose refers to that amount of an antibody or a fragment thereof sufficient to result in a healthful benefit in the treated subject. Formulations and methods of administration that can be employed when the pharmaceutical composition contains an antibody of the present invention are described below.

It is to be further understood that a cocktail of different monoclonal antibodies, such as a mixture of the specific monoclonal antibodies described herein or their binding fragments, may be administered, if necessary or desired, to alleviate cancers. Indeed, using a mixture of monoclonal antibodies, or binding fragments thereof, in a cocktail to target several antigens, or different epitopes, on cancer cells, is an advantageous approach, particularly to prevent evasion of tumor cells and/or cancer cells due to downregulation of one of the antigens.

Pharmaceutical compositions for use in accordance with the present invention can be formulated in conventional manner using one or more pharmaceutically acceptable carriers or excipients.

The antibodies or fragments thereof can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing and/or dispersing agents. Alternatively, the antibody can be in lyophilized powder form for constitution with a suitable vehicle, e.g., sterile pyrogen-free water, before use.

Toxicity and therapeutic efficacy of the antibody or fragment, or the therapeutic moiety conjugated thereto can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD/ED.

Antibodies or therapeutic moieties that exhibit large therapeutic indices are preferred. While antibodies or moieties that exhibit toxic side effects can be used, care should be taken to design a delivery system that targets such antibodies or moieties to the site of affected tissue in order to minimize potential damage to uninfected cells and, thereby, reduce side effects.

The data obtained from the cell culture assays and animal studies can be used in formulating a range of dosages for use in humans. The dosage of such antibodies lies preferably within a range of circulating plasma concentrations that include the ED50 with little or no toxicity. The dosage can vary within this range depending upon the dosage form employed, the route of administration utilized and types and amounts of the therapeutic moiety conjugated. For any antibody used in the method of the invention, the effective dose can be estimated initially from cell culture assays. A dose can be formulated in animal models to achieve a circulating plasma concentration range that includes the IC50 (i.e., the concentration of the test antibody that achieves a half-maximal inhibition of symptoms) as determined in cell culture. Such information can be used to more accurately determine useful doses in humans. Levels in plasma can be measured, for example, by high performance liquid chromatography.

While depending on the conditions and age of the subject and/or administration route, one skilled in the art can select an appropriate dose of the pharmaceutical composition of the present invention. For example, the pharmaceutical composition of the present invention is administered in an amount such that the antibody according to the present invention is administered to the subject in a day in an amount of about 3 to about 15 mcg per kg body weight of subject, and preferably of about 10 to about 15 mcg per kg body weight of subject. The administration interval and times can be selected in consideration of the condition and age of the subject, administration route, and response to the pharmaceutical composition. For example, the pharmaceutical composition can be administered to the subject one to 5 times, preferably 1 times a day for 5 to 10 days.

In another aspect, when the composition comprising the radioisotope labeled antibody is parenterally administered, the administrative dose for a single adult is 0.1 mCi/kg to 1.0 mCi/kg, preferably 0.1 mCi/kg to 0.5 mCi/kg, and more preferably 0.4 mCi/kg at once.

The pharmaceutical composition can be administered systemically or locally. It is preferably administered in a targeting delivery manner so as to deliver the active component to an affected site.

In particular embodiments, the methods and compositions of the present invention are used for the treatment or prevention of the cancer together with one or a combination of chemotherapeutic agents including, but not limited to, methotrexate, taxol, mercaptopurine, thioguanine, cisplatin, carboplatin, mitomycin, bleomycin, doxorubicin, idarubicin, daunorubicin, dactinomycin, vinblastine, vincristine, vinorelbine, paclitaxel, and docetaxel.

With respect to radiation therapy, any radiation therapy protocol can be used depending upon the type of the cancer to be treated. For example, but not by way of limitation, X-ray radiation can be administered. Gamma ray emitting radioisotopes, such as radioactive isotopes of radium, cobalt, and other elements may also be administered to expose tissues.

In another embodiment, chemotherapy or radiation therapy is administered, preferably at least an hour, five hours, 12 hours, a day, a week, a month, and more preferably several months (e.g., up to three months) subsequent to using the methods and compositions containing the antibody of the present invention. The chemotherapy or radiation therapy administered prior to, concurrently with, or subsequent to the treatment using the methods and compositions according to the present invention can be administered by any method known in the art.

In another embodiment, the present invention also provides the use of the antibody of the present invention in manufacturing a pharmaceutical composition for treating or preventing a disease associated with CDH3. In particular, the present invention further provides a use of radio-labeled antibody of the present invention for manufacturing a pharmaceutical composition for treating or preventing a cancer.

Alternatively, the present invention further provides the antibody of the present invention for use in treating or preventing a disease associated with CDH3. In particular, the radio-labeled antibody of the present invention for use in radioimmunotherapy for cancer is also provided.

Alternatively, the present invention further provides a method or process for manufacturing a pharmaceutical composition for treating or preventing a disease associated with CDH3, wherein the method or process comprises step for formulating a pharmaceutically or physiologically acceptable carrier with the antibody of the present invention as active ingredients. In particular, the present invention further provides a method or process for manufacturing a pharmaceutical composition for treating or preventing a cancer, wherein the method or process comprises step for formulating a pharmaceutically or physiologically acceptable carrier with the radio-labeled antibody of the present invention as active ingredients.

In another embodiment, the present invention also provides a method or process for manufacturing a pharmaceutical composition for treating or preventing a disease associated with CDH3, wherein the method or process comprises step for admixing an active ingredient with a pharmaceutically or physiologically acceptable carrier, wherein the active ingredient is the antibody of the present invention. In particular, the present invention further provides a method or process for manufacturing a pharmaceutical composition for treating or preventing a cancer, wherein the method or process comprises step for admixing the radio-labeled antibody of the present invention with a pharmaceutically or physiologically acceptable carrier.

In further embodiment, the present invention provides the antibody of the present invention for use in bioimaging or immunoscintigraphy for cancer within a subject to be diagnosed. Alternatively, the present invention provides use of the antibody of the present invention for manufacturing a diagnostic agent for bioimaging or immunoscintigraphy for cancer within a subject. The present invention further provides a method or process for manufacturing a diagnostic agent for bioimaging or immunoscintigraphy for cancer within a subject, wherein the method or process comprises step for admixing the antibody of the present invention with a pharmaceutically or physiologically acceptable carrier.

All prior art references cited herein are incorporated by reference in their entirety.

EXAMPLES

Below, the present invention is further explained based on Examples.
Materials and Methods
Antibody Production.

CDH3 gene encoded extracellular domain (SEQ ID NO: 3) was amplified from cDNA pool derived from cancer cells. The product was cloned into the pcDNA3.1 (Invitrogen, CA). To produce CDH3-specific antibody, mice were immunized subcutaneously with the domain expression vector (17.5 mcg/injection) every two weeks for a month. After the confirmation of the titer of antisera, spleenocytes were extracted from the mice and fused to myeloma cells to prepare hybridomas. We screened the hybridomas which can recognize native CDH3 antigen on the surface of the cancer cells. Through the screening, it was revealed that hybridoma clone #6 produced antigen-specific antibody at high level, therefore this clone was selected to produce antibody for further experiments. The hybridoma clone #6 was used to inject intraperitoneally into mice. The ascites was recovered after 2 to 3 weeks. Finally antibody was purified from the ascites using Protein A column (GE Healthcare, NJ).
Cell Culture.

Six cancer cell lines were used: EBC-1, H1373 and H358 as non-small cell lung cancer line; KLM-1 and MIAPaCa-2 as pancreatic cancer line; SW948 as colorectal cancer line. All cell lines were obtained from American Type Culture Collection (Manassasm, Va.), and were maintained in EMEM (EBC-1, MIAPaCa-2), RPMI (H358, KLM-1, H1373) and L-15 (SW948) supplemented with 10% fetal bovine serum (FBS) and 1% penicillin/streptomycin at 37 degrees C. in a humidified atmosphere of 5% $CO_2$.
Flow Cytometer H358, KLM-1 and MIAPaCa-2 were maintained in each recommended culture media until early-confluency. The cells were subsequently dissociated with Cell Dissociation Solution (SIGMA, MO) to avoid denaturing of cell surface antigen. Cells were suspended with PBS (1×107 cells/mL) and incubated with test antibody (50 mcg/mL) for 1 h at 4 degrees C. After washing twice with PBS, cells were mixed with 20 mcg/mL of Alexa Fluor488 goat anti-mouse IgG (H+L) (Invitrogen, CA) containing 7AAD (2.5 mcg/mL) and incubated for 30 min at 4 degrees C. in dark. Binding mode and specificity of test antibody was evaluated by FACS Calibur (Becton Dickinson, NJ) according to manufacturer's instruction.
Radiolabeling.

Anti-CDH3 mouse monoclonal antibody produced by hybridoma clone #6 (clone 6), the chimeric antibody of clone 6 (ch-#6) produced by 293T and control antibodies, normal mouse IgG1 (Nordic immunological laboratories, Tiburg, The Netherlands) and normal human IgG were labeled with two different isotopes; Indium-111 ($^{111}$In) and Yttrium-90 ($^{90}$Y). Antibody was labeled with $^{111}$In and $^{90}$Y via a bifunctional metal ion chelating agent, p-SCN-Bn-DTPA or p-SCN-Bn-CHX-A"-DTPA (Macrocyclics, Dallas, Tex., USA). One milligram of antibody was conjugated to these chelators in dimethylformamide at a molar ratio of 1:5. After incubation at 37 degrees C. for 20 h, antibody-chelator complexes were purified using Biospin Column 6 (Bio-Rad, Tokyo, Japan). $^{111}$InCl$_3$ (Nihon Medi-Physics, Hyogo, Japan) and $^{90}$YCl3 (QSA Global, Brauschweig, Germany) were respectively pre-incubated with 0.25 M acetic acid (pH 5.5) for 5 minutes at room temperature in parallel. To obtain $^{111}$In- and $^{90}$Y-labeled antibodies, the antibody-chelator complexes were incubated with the preincubated $^{111}$InCl$_3$ and $^{90}$YCl$_3$ solution respectively for 1 hour at 37 degrees C. Labeled antibody was purified using Biospin Column 6 according to manufacture's instructions. It was confirmed that degradation of these antibodies was not observed during labeling processes.

Xenograft Models.

Animal care and treatment was performed in accordance with the guidelines of animal use and animal committee of the Gunma University. 100 mcL of EBC1, SW948, KLM-1 and H1373 cell suspension ($1\times10^7$ cells) were inoculated subcutaneously into the right flank of female 3- to 5-week-old nude mice (Charles River Laboratories Japan Inc. Yokohama, Japan). These mice were kept for several weeks to develop the tumors. The established tumors were isolated from tumor-bearing mice and dissected into cubic tissue fragments 2 mm on a side. These fragments were transplanted serially into nude mice. After the transplantation, these mice were kept until the average tumor volume reached 100-600 mm3.

[Biodistribution Study.

Nude mice bearing established human lung cancer tumor EBC-1 were randomly selected and assigned to two groups. The mice were injected with Alexa647-labeled and $^{111}$In-labeled (0.5 mCi/mg) antibodies intravenously. For fluorescence-based study, the biodistribution of Alexa647-labeled antibodies was evaluated with IVIS 200 bioimaging system (Caliper Life Sciences, MA) at 48 hours after treatment. For radioisotope-based study, the grafted tumors were isolated, along with blood, liver, kidney, intestines, stomach, spleen, pancreas, lung, heart, muscle and bones respectively at 3, 24, 48 and 72 hours after injection. All tissues were weighed and counted the radioactivity on a gamma-well counter, and the percentage of injected dose per gram (% ID/g) was determined. In particular, $^{111}$In-labeled clone 6 was analyzed at 48 hours using nude mice bearing established tumors (EBC-1, SW948, KLM-1 and H1373) respectively.

Radiotherapy (Single Administration).

Xenograft mice were randomly assigned to three different treatment groups. $^{90}$Y-labeled antibodies (4-10 mCi/mg) were prepared as described above. The mice were injected intravenously with $^{90}$Y-labeled clone 6 or $^{90}$Y-labeled normal mouse IgG1 as control. Radioactivity of injected antibodies was adjusted to 100 mcCi per animal. Body weight and tumor volume of the treated-xenograft mice were monitored for 4 weeks after $^{90}$Y-labeled antibody injection. The tumor volume (mm$^3$) was calculated using following formula: (the shortest diameter)$^2\times$(the longest diameter)$\times$0.5.

Radiotherapy (Twice Administration).

SW948 xenograft mice were randomly assigned to four different treatment groups. Antibodies were conjugated to p-SCN-Bn-DTPA for radiolabeling with $^{90}$Y. $^{90}$Y-labeled antibodies (4-10 mCi/mg) were prepared as described above. The mice were injected intravenously with $^{90}$Y-labeled clone 6 or $^{90}$Y-labeled normal IgG1 as control. Second injection was performed with $^{90}$Y-labeled clone 6 after 14 days of the first injection. Radioactivity of injected antibodies was adjusted to 100 mcCi per animal. Body weight and tumor volume of the treated-xenograft mice were monitored for 7 weeks after first $^{90}$Y-labeled antibody injection. The tumor volume (mm3) was calculated using following formula: (the shortest diameter)$^2\times$(the longest diameter)$\times$0.5.

HE Staining.

Isolated tumors were embedded with Lab-Tek OCT compound (Sakura Finetek USA, CA) on dry-ice to prepare frozen tissue section. The frozen sections were washed with distilled water to remove OCT compound, and treated with xylene for 5 min in twice. To wash the excessive xylene and re-hydrate, the sections were rinsed with 100%, 90%, 80%, 70% and 50% ethanol for 10 sec, respectively. Slide sections were immersed in Mayer's Hematoxilin (Muto Pure Chemicals, Japan) for 5 min, and washed excessive Hematoxilin with flowing water. Next, dehydration was performed using 50%, 70%, 80%, 90% and 100% ethanol after 1% Eosin Y (Muto Pure Chemicals, Japan) treatment. Finally the sections were treated with xylene for 5 min in thrice, serially enclosed by Malinol (DAIDO SANGYO, Japan).

Amino Acids Sequence.

Total RNAs were extracted from hybridoma Clone #6 using RNeasy Mini Kit (QIAGEN). cDNA was synthesized from the total RNA using SuperScript II Reverse Transcriptase (Invitrogen). The sequences of variable regions of monoclonal antibodies were amplified using NovaTaq DNA polymerase (Novagen) and Mouse Ig-Primer Set (Novagen). The sequence of variable regions of monoclonal antibodies were amplified using 5' primer; MuIgVH5'-B; 5'-GGGAAT-TCATGRAATGSASCTGGGTYWTYCTCTT-3' (SEQ ID NO:4) for heavy chain, and MuIg kappa VL5'-G; 5'-ACT-AGTCGACATGAAGTTGCCTGTTAGGCT-GTTGGTGCT-3' (SEQ ID NO: 5), 5'-ACTAGTCGACATG-GATTTWCARGTGCAGATTWTCAGCTT-3' (SEQ ID NO: 6), 5'-ACTAGTCGACATGGTYCTYATVTCCT-TGCTGTTCTGG-3' (SEQ ID NO: 7) and 5'-ACTAGTCGA-CATGGTYCTYATVTTRCTGCTGCTATGG-3' (SEQ ID NO: 8) for light chain of Clone #6 and 3' primer; MuIg-GVH3'-2; 5'-CCCAAGCTTCCAGGGRCCARKGGATA-RACIGRTGG-3' (SEQ ID NO: 9) for heavy chain and MuIg kappa VL3'-1; 5'-CCCAAGCTTACTGGATGGTGGGAA-GATGGA-3' (SEQ ID NO: 10) for light chain. PCR products were cloned into pCR2.1-TOPO (Invitrogen). Insert regions were sequenced and the sequence of the variable region (except for the signal sequence) of Clone #6 were determined.

Following symbols are used for the different nucleotides in the primer sequences;

B as C, G or T, D as A, G or T, H as A, C or T, I as inosine, K as G or T, M as A or C, R as A or G, S as C or G, V as A, C or G, W as A or T and Y as C or T.

Chimeric Mouse/Human Antibody

Chimeric mouse/human antibody ch-#6 based on the mouse monoclonal antibody Clone #6, was prepared using the GS Gene Expression System (Lonza, Switzerland). Both heavy chain and light chain were amplified by overlap extension polymerase chain reaction. The variable region of heavy chain was amplified by PCR using primers of SEQ ID NO: 23 and 24. The constant region of human IgG1 was amplified by PCR using primers of SEQ ID NO: 27 and 28. These two PCR products contained common sequence in terminal for overlap extension. Then gene of heavy chain was amplified with these two PCR products by overlap extension PCR using primers of SEQ ID NO: 31 and 28. In same manner, the variable region of light chain was amplified by PCR using primers of SEQ ID NO: 25 and 26. The constant region of human kappa was amplified by PCR using primers of SEQ ID NO: 29 and 30. Gene of light chain was amplified with these two PCR products containing common sequence in terminal by overlap extension PCR using primers of SEQ ID NO: 32 and 30. Genes corresponding to each of the variable regions of Light chain and Heavy chain were amplified with constant region of human kappa (SEQ ID NO: 19 encoding SEQ ID NO: 21) and human IgG1 (SEQ ID NO: 20 encoding SEQ ID NO: 22), respectively, by PCR and cloned into an antibody expression vector pEE12.4 and pEE6.4, respectively, using the restriction enzyme HindIII and EcoRI. These two single gene vectors (SGV) were digested with the restriction enzyme NotI and PvuI. The digested heavy chain SGV DNA contains the hCMV-MIE promoter-heavy chain-SV40 transcription unit, and the digested light chain SGV DNA contains the GS transcription unit and the hCMV-MIE, promoter-light chain expression cassette. Both purified fragments were ligated to construct the double gene expression vector. *E. coli* cells were transformed with the vector and then the vector was prepared. The vector expressing both H-chain and L-chains was transfected into 293T cells. The medium was exchanged with serum-free medium (DMEM; GIBCO, 11965-092), and the chimeric antibody contained in the culture supernatant was purified via Protein A column.

the clone 6 and ch-#6 was increased time-dependently (data not shown). As shown in FIG. 3A-E, normal tissues displayed quite low levels of uptake, consistent with the exclusive expression profile of CDH3. As shown in biodistribution study, the uptake of clone 6 was observed in CDH3 presenting tumor-specific manner. Therefore, the antibody has an ideal property to develop as a radioisotope-labeled antibody medicine.

TABLE 1

Primer set for preparation of ch-#6

| SEQ ID NO | primer | sequence |
|---|---|---|
| 23 | HindIIICDH3#6VH-f | AAGCTTGCCGCCACCATGAAATGGAGCTGGGTTATTC |
| 24 | CDH3#6VHCH-r | CCCTTGGTGGAGGCTGCAGAGACAGTGACC |
| 25 | HindIIICDH3#6VL-f | AAGCTTGCCGCCACCATGGATTTACAGGTGCAGATTATCAGC |
| 26 | CDH3#6VLkappa-r | CGTTTTAATTCCAGCTTGGTGCCTCCACC |
| 27 | CDH3#6VHCH-f | CTCTGCAGCCTCCACCAAGGGCCCATCGG |
| 28 | EcoRIIgG1-r | TTATTAGAATTCCTATCATTTACCCGGAGACAGGGAGAGGC |
| 29 | CDH3#6VLkappa-f | ACCAAGCTGGAATTAAAACGTACTGTTGC |
| 30 | EcoRIKappa-r | TTATTAGAATTCCTATCAACATTCACCACGATTAAAAGATTTAGTAACAGG |
| 31 | HindIIIB72.3CDH3#6H-f | CACGAAGCTTGCCGCCACCATGGAATGGAGCTGGGTGTTCCTGTTCTTTCTGTCCGTGACCACAGGCGTGCATTCTCAGGTCCAACTGCAGCAGCCTGGG |
| 32 | HindIIIB72.3CDH3#6L-f | ACGAAGCTTGCCGCCACCATGTCTGTGCCTACCCAGGTGCTGGGACTGCTGCTGCTGTGGCTGACAGACGCCCGCTGTCAAATTGTTCTCACCCAGTCTC |

Results.

First, to evaluate the specificity of anti-CDH3 antibodies, the expression of CDH3 was determined in several cell lines. CDH3 antigen was presented on the surface of H358 and KLM-1, but not on MIAPaCa-2 (FIG. 1). The antibodies, which displayed satisfactory reactivity with H358 and KLM-1 but not with MIAPaCa-2, were screened using flowcytometer. As shown in FIG. 1, all screened anti-CDH3 antibodies recognized native CDH3 protein correctly and specifically.

Figure 6:
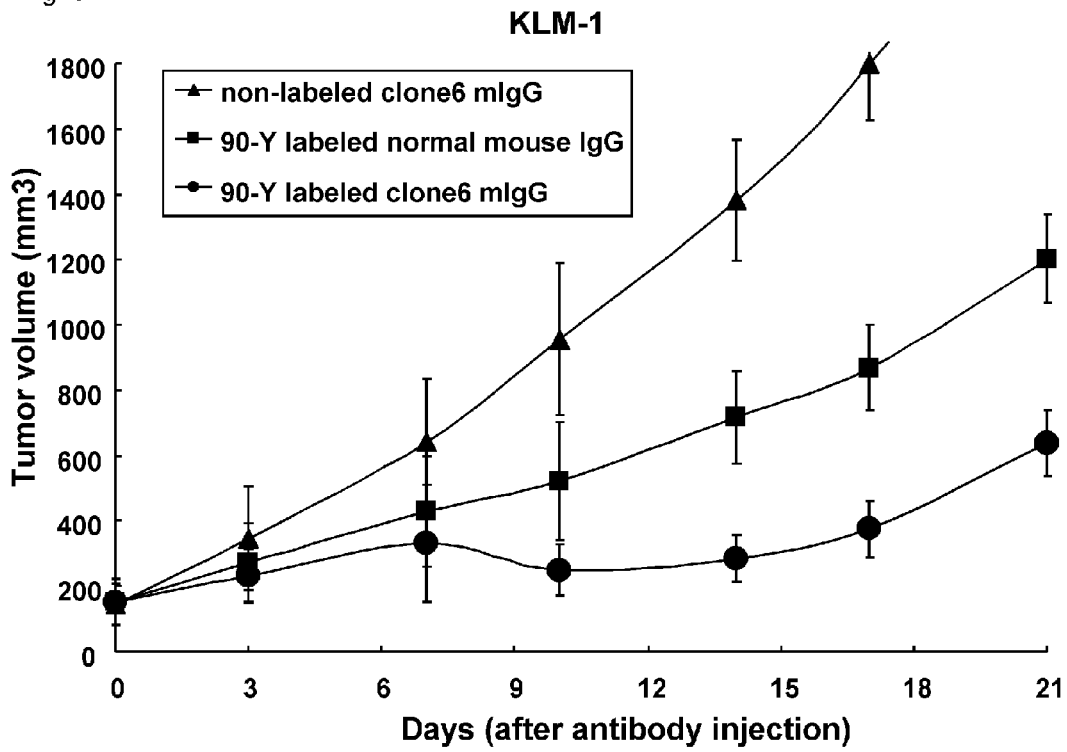
FIG. 6 shows that single administration of $^{90}$Y-labeled anti-CDH3 antibody (clone#6) suppresses the growth of KLM-1 cells grafted in nude mice.
Figure 7:
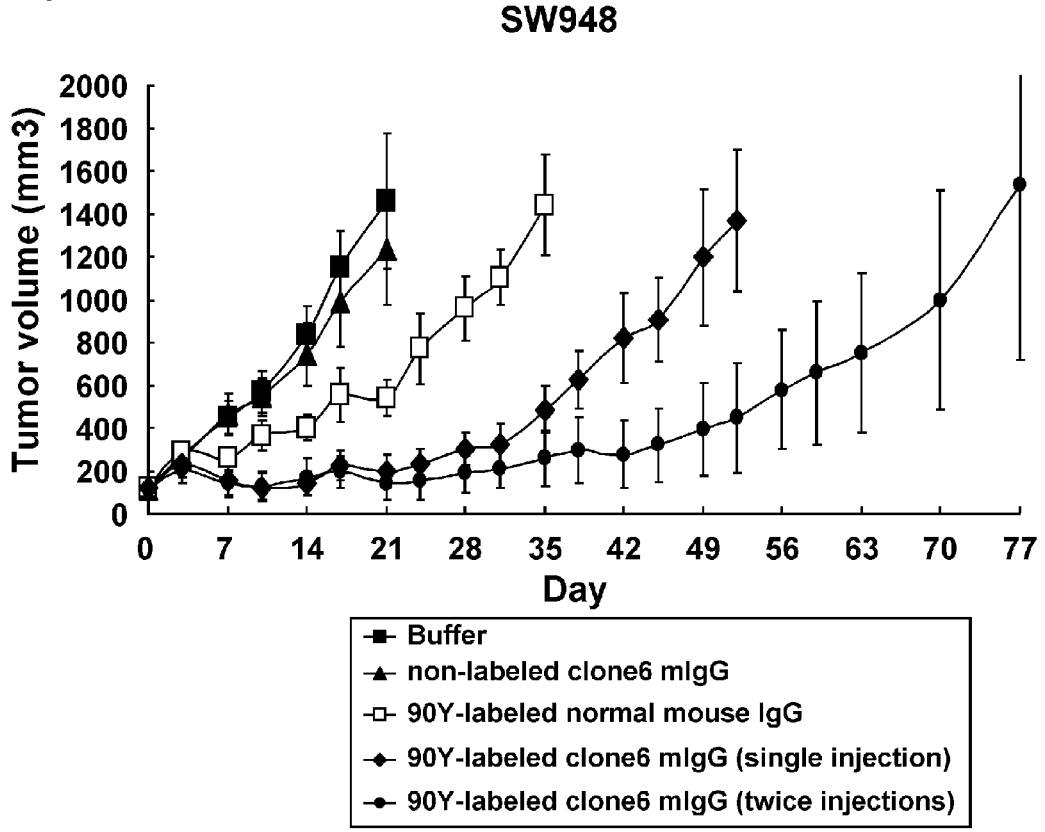
FIG. 7 shows that both single and twice administration of $^{90}$Y-labeled anti-CDH3 antibody (clone#6) suppresses the growth of SW948 cells grafted in nude mice.
Figure 8:
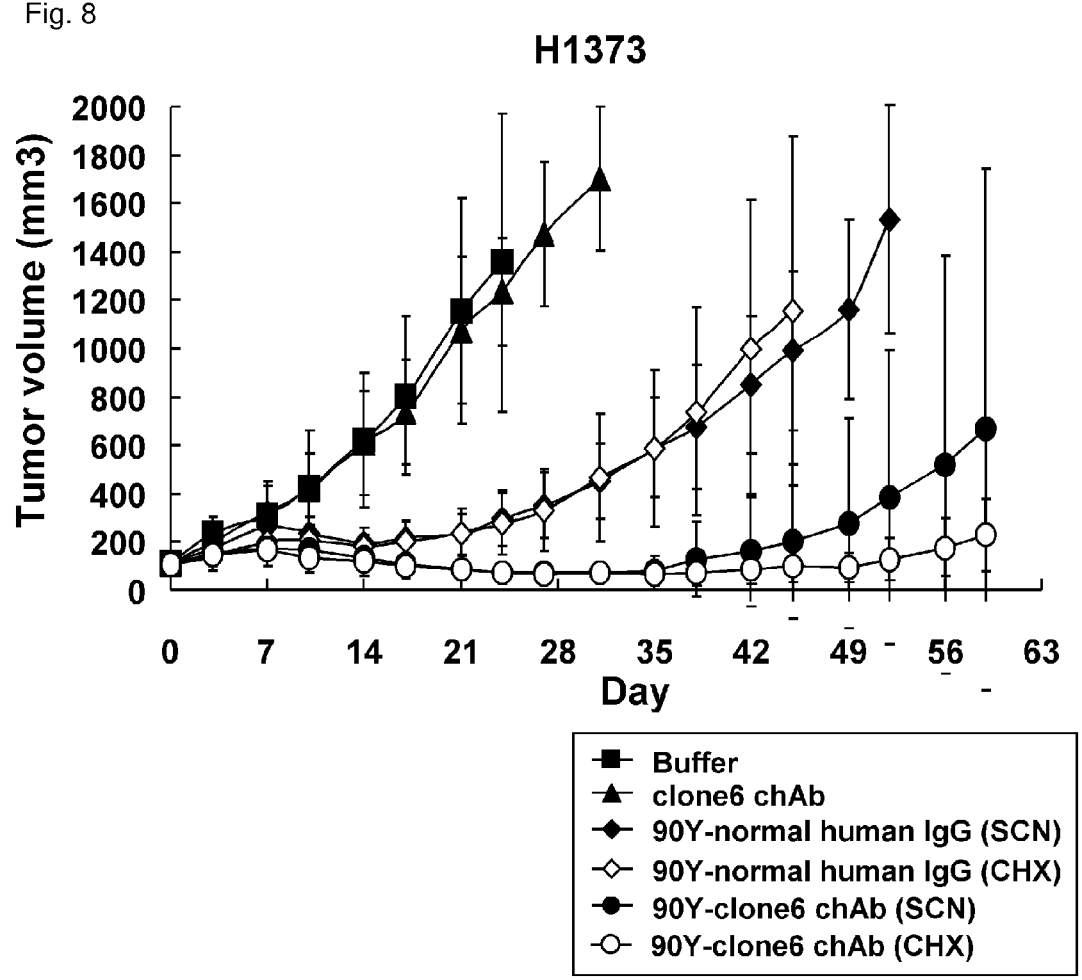
FIG. 8 shows that single administration of $^{90}$Y-labeled anti-CDH3 chimeric antibody (ch-#6) suppresses the growth of KLM-1 cells grafted in nude mice. CHX and SCN represent p-SCN-Bn-CHX-A"-DTPA and p-SCN-Bn-DTPA, respectively. Antibodies are conjugated to these bifunctional chelators for radiolabeling with $^{90}$Y.

Second, the biodistribution of anti-CDH3 antibodies was checked using xenograft models. Alexa647-labeled antibodies #4 and #6 were accumulated in tumors at very high level compared to other clones and control antibody (FIG. 2A). #6 was selected for radiotherapy with $^{90}$Y because $^{111}$In-labeled #6 showed more fast blood clearance and high tumor targeting without unexpected accumulating in normal organs compared with the others (FIG. 2B-F). The peak uptake of the clone 6 into the tumor was 32.0+/−3.5% ID/g (EBC-1), 21.4+/−2.3% ID/g (SW948), 24.2+/−1.2% ID/g (KLM-1), 23.8+/−3.1% ID/g (H1373) respectively at 48 h after injection (FIG. 3A-D). In the same way, the peak uptake of the chimeric antibody of clone 6 named ch-#6 into the tumor was 38.0+/−3.2% ID/g (H1373) at 48 h after injection (FIG. 3E). In contrast, the uptake of control IgG never exceeded 10% ID/g in every mouse (FIG. 3A-E). This tumor-specific uptake of Third, radiotherapy with $^{90}$Y-labeled clone 6 and ch-#6 was performed using xenograft mice. All tumors were drastically decreased growth rate by radiation from yttrium-90 conjugated with the clone 6 (FIGS. 4A, 5A, 6, 7) and ch-#6 (FIG. 8). On the other hand, $^{90}$Y-labeled control antibody showed no effect on tumor growth (FIGS. 4A, 5A, 6, 7, 8). Therefore, this therapeutic effect seemed to depend on the antigen-antibody reaction. Treatment for EBC-1 (lung cancer) tumors displayed stable disease for one month by only single injection (FIG. 4A). Tumors were isolated and performed HE staining after the radiotherapy. As shown in FIG. 4B, tumor cell number was drastically decreased and the marked fibrosis was observed by the treatment with $^{90}$Y-labeled clone 6. It is notable that no fibrosis was observed in tumors treated with $^{90}$Y-labeled control IgG (FIG. 4B). Likewise, SW948 (colon cancer) tumors showed partial response by the treatment (FIG. 5). The transplanted tumors almost disappeared in each mouse after 21 days of injection of $^{90}$Y-labeled clone 6 (FIG. 5B). While KLM-1 (pancreatic cancer) tumors showed stable disease or slightly progressive disease status by the treatment (FIG. 6). But the treatment with $^{90}$Y-labeled clone 6 was efficacious in comparison to that of non-labeled antibody. The twice administration of $^{90}$Y-labeled clone 6 was more efficacious than the single administration in every mouse (FIG. 7). Furthermore, $^{90}$Y-labeled ch-#6 that chimeric antibody of clone 6 shows high efficacy compared to the controls (FIG. 8). CHX and SCN in FIG. 8 represent linkers described in Materials and Methods.

Taken together, anti-CDH3 antibody clone 6 and ch-#6 conjugated yttrium-90 exerted remarkable therapeutic effects against these tumors. Therefore CDH3 is attractive therapeutic target for these tumors and anti-CDH3 antibody is useful-therapeutic drug candidate for this type of treatment.

Finally, the amino acid sequence of mouse Ig H-chain variable regions and L-chain variable regions were determined as follows:

Clone #6, H-chain variable region
(except for the signal sequence):
(SEQ ID NO: 11)
QVQLQQPGAELVKPGTSVKLSCKSSGYTFTSWIHWVKQRPGHGLEWIGEI

DPSDNYTYYNQNFKGKATLTIDKSSSTAYMQLNSLTSEDSAVFYCARSGY

GNLFVYWGQGTLVTVSA;
and

Clone #6, L-chain variable region
(except for the signal sequence):
(SEQ ID NO: 12)
QIVLTQSPAIMSSSPGEKVTMSCSATSSVTYMYWYQQKPGSSPKPWIFRT

SNLASGVPTRFSGSGSGTSYSLTISSMEAEDAATYYCQHYHIYPRTFGGG

TKL.

The CDR (complementarity determining region) sequences of the antibodies were determined by the Kabat definition as follows:

| Clone #6, | |
|---|---|
| SYWIH as VH CDR1, | (SEQ ID NO: 13) |
| EIDPSDNYTYYNQNFKG as VH CDR2 and | (SEQ ID NO: 14) |
| SGYGNLFVY as VH CDR3, | (SEQ ID NO: 15) |
| SATSSVTYMY as VL CDR1, | (SEQ ID NO: 16) |
| RTSNLAS as VL CDR2 and | (SEQ ID NO: 17) |
| QHYHIYPRT as VL CDR3. | (SEQ ID NO: 18) |

INDUSTRIAL APPLICABILITY

The present invention is based, at least in part, on the discovery that a cancer expressing CDH3 can be treated with radioisotope labeled anti-CDH3 antibody in vivo. CDH3 was identified by the present inventors as a gene strongly expressed in pancreatic, lung, colon, prostate, breast, gastric or liver cancers. Thus, treatment of a cancer, for example, pancreatic, lung, colon, prostate, breast, gastric or liver cancer is conveniently carried out using anti-CDH3 antibodies labeled with radioisotope label.

The invention claimed is:

1. An antibody or a fragment thereof, which specifically recognizes a polypeptide having the amino acid sequence as shown in SEQ ID NO: 3, and which comprises an H (heavy) chain V (variable) region comprising a complementarity determining region (CDR) having the amino acid sequences shown in SEQ ID NOs: 13, 14 and 15 and an L (light) chain V region comprising a CDR having the amino acid sequences shown in SEQ ID NOs: 16, 17 and 18.

2. The antibody or fragment thereof according to claim 1, wherein the antibody is selected from the group consisting of a mouse antibody, a chimeric antibody, a humanized antibody, an antibody fragment, and single chain antibody.

3. The antibody or fragment thereof according to claim 2, wherein the antibody comprises an H chain having the amino acid sequence shown in SEQ ID NO: 11 and/or an L chain having the amino acid sequence shown in SEQ ID NO: 12.

4. The antibody or fragment thereof according to claim 2, wherein the chimeric antibody comprises an H chain V region having the amino acid sequence shown in SEQ ID NO: 11.

5. The antibody or fragment thereof according to claim 2, wherein the chimeric antibody comprises an L chain V region having the amino acid sequence shown in SEQ ID NO: 12.

6. The antibody or fragment thereof according to claim 3, wherein the chimeric antibody comprises an H chain V region having the amino acid sequence shown in SEQ ID NO: 11 and an L chain V region having the amino acid sequence shown in SEQ ID NO: 12.

7. The antibody or fragment thereof according to claim 1, wherein the antibody is a humanized antibody.

8. The antibody or fragment thereof according to claim 7, wherein the humanized antibody further comprises a human antibody FR (framework) region and/or a human antibody C region.

9. The antibody or fragment thereof according to claim 1, which is conjugated with a cytotoxic, a therapeutic agent, a radioisotope label or a fluorescent label.

10. The antibody or fragment thereof according to claim 9, wherein the radioisotope label is selected from 90yttrium ($^{90}$Y) and 111indium ($^{111}$In).

11. A method for treating a tumor expressing CDH3 in a subject, comprising administering to the subject an effective amount of the antibody or fragment according to claim 1, wherein the antibody is conjugated with a radioisotope label.

12. A method for diagnosis of a tumor expressing CDH3 comprising:
(a) contacting a sample or a specimen form a subject with the antibody or fragment according to claim 1;
(b) detecting the CDH3 protein in the sample or specimen; and
(c) judging whether or not the subject has a tumor based on the relative abundance of the CDH3 protein compared to a control.

13. A pharmaceutical composition comprising the antibody or fragment according to claim 9 and a pharmaceutically acceptable carrier or excipient.

14. A kit comprising the antibody or fragment according to claim 1.

15. A method for treating a tumor expressing CDH3 in a subject, comprising administering to the subject an effective amount of the antibody or fragment according to claim 10.

16. A pharmaceutical composition comprising the antibody or fragment according to claim 10 and a pharmaceutically acceptable carrier or excipient.

* * * * *

UNITED STATES PATENT AND TRADEMARK OFFICE
CERTIFICATE OF CORRECTION

PATENT NO. : 8,435,749 B2  Page 1 of 1
APPLICATION NO. : 13/001869
DATED : May 7, 2013
INVENTOR(S) : Togashi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 149 days.

Signed and Sealed this
Eighth Day of September, 2015

Michelle K. Lee
*Director of the United States Patent and Trademark Office*

SEQUENCE LISTING

```
<160> NUMBER OF SEQ ID NOS: 32

<210> SEQ ID NO 1
<211> LENGTH: 4276
<212> TYPE: DNA
<213> ORGANISM: Homo sapiens
<220> FEATURE:
<223> OTHER INFORMATION: placental cadherin, P-cadherin, CDH3

<400> SEQUENCE: 1
tgcgttttaa aaattgtctt tatttacatt ttacagaaag ttgagaaagt gttatttata      60 tgggggtag gggtgctgga gattatgaga ctaataacaa ccctcttagc tcgcaccctt     120
tggcaccact acagcttcca aactctggga ctttctcgac tagcttccct ttgtttagct     180
gtgaaatgga agaagcggtc cgggtgtggc ggctcatgcc tgtaacctga gcactctggg     240
aggcggagga tcgcttgagt ccagaagttc aagaccagct tgggcaacat agggtgaccc     300
tccaccctcc ccccgcccca ccatcgct acaaaaaatt tttaaaaatt agcccgggtgt     360 ggtggcgcaa gcctgtagtc tcagcgggag ctgagggagg agaatcgctt cagcccggga     420
ggtcgaggct gtagtgagcc gagatcgcgc tactgcactc ctgggcgaca gagcgagacc     480
ctgtctccaa aaaaaaaaaa aaaagaaaaa agaggaagtt gtatccaatt cagaaacgcg     540
gtccttcggg acctgctagt tttatacccc ggaggatcct ccccggcggg ctggcacggg     600
aggtggagaa agaggcttgg gcggcccgc tgtagccgcg tgtgggagga cgcacgggcc     660
tgcttcaaag ctttgggata acagcgcctc cggggataa tgaatgcgga gcctccgttt     720
tcagtcgact tcagatgtgt ctccactttt ttccgctgta gccgcaaggc aaggaaacat     780
ttctcttccc gtactgagga ggctgaggag tgcactgggt gttcttttct cctctaaccc     840
```

-continued

```
agaactgcga gacagaggct gagtccctgt aaagaacagc tccagaaaag ccaggagagc    900
gcaggagggc atccgggagg ccaggagggg ttcgctgggg cctcaaccgc acccacatcg    960
gtcccacctg cgagggggcg ggacctcgtg gcgctggacc aatcagcacc cacctgcgct   1020
cacctggcct cctcccgctg gctcccgggg gctgcggtgc tcaaaggggc aagagctgag   1080
cggaacaccg gcccgccgtc gcggcagctg ctttcacccct ctctctgcag ccatggggct   1140
ccctcgtgga cctctcgcgt ctctcctcct tctccaggtt tgctggctgc agtgcgcggc   1200
ctccgagccg tgccgggcgg tcttcaggga ggctgaagtg accttggagg cgggaggcgc   1260
ggagcaggag cccggccagg cgctggggaa agtattcatg ggctgccctg ggcaagagcc   1320
agctctgttt agcactgata atgatgactt cactgtgcgg aatggcgaga cagtccagga   1380
aagaaggtca ctgaaggaaa ggaatccatt gaagatcttc ccatccaaac gtatcttacg   1440
aagacacaag agagattggg tggttgctcc aatatctgtc cctgaaaatg caagggtcc    1500
cttcccccag agactgaatc agctcaagtc taataaagat agagacacca agattttcta   1560
cagcatcacg gggccggggg cagacagccc ccctgagggt gtcttcgctg tagagaagga   1620
gacaggctgg ttgttgttga ataagccact ggaccgggag gagattgcca agtatgagct   1680
cttttggccac gctgtgtcag agaatggtgc ctcagtggag gaccccatga acatctccat   1740
catcgtgacc gaccagaatg accacaagcc caagtttacc caggacacct tccgagggag   1800
tgtcttagag ggagtcctac caggtacttc tgtgatgcag gtgacagcca cggatgagga   1860
tgatgccatc tacacctaca atggggtggt tgcttactcc atccatagcc aagaaccaaa   1920
ggacccacac gacctcatgt tcaccattca ccggagcaca ggcaccatca gcgtcatctc   1980
cagtggcctg gaccgggaaa aagtccctga gtacacactg accatccagg ccacagacat   2040
ggatgggac ggctccacca ccacggcagt ggcagtagtg gagatccttg atgccaatga   2100
caatgctccc atgtttgacc cccagaagta cgaggcccat gtgcctgaga atgcagtggg   2160
ccatgaggtg cagaggctga cggtcactga tctggacgcc cccaactcac cagcgtggcg   2220
tgccacctac cttatcatgg gcggtgacga cggggaccat tttaccatca ccacccaccc   2280
tgagagcaac cagggcatcc tgacaaccag gaagggtttg gattttgagg ccaaaaacca   2340
gcacaccctg tacgttgaag tgaccaacga ggccccttttt gtgctgaagc tcccaacctc   2400
cacagccacc atagtggtcc acgtggagga tgtgaatgag gcacctgtgt ttgtcccacc   2460
ctccaaagtc gttgaggtcc aggagggcat ccccactggg gagcctgtgt gtgtctacac   2520
tgcagaagac cctgacaagg agaatcaaaa gatcagctac cgcatcctga gacccagc    2580
agggtggcta gccatggacc cagacagtgg gcaggtcaca gctgtgggca ccctcgaccg   2640
tgaggatgag cagtttgtga ggaacaacat ctatgaagtc atggtcttgg ccatggacaa   2700
tggaagccct cccaccactg gcacgggaac ccttctgcta acactgattg atgtcaatga   2760
ccatggccca gtccctgagc ccgtcagatc accatctgc aaccaaagcc ctgtgcgcca   2820
ggtgctgaac atcacggaca aggacctgtc tccccacacc tccccttttcc aggcccagct   2880
cacagatgac tcagacatct actgacggc agaggtcaac gaggaaggtg acacagtggt   2940
cttgtccctg aagaagttcc tgaagcagga tacatatgac gtgcacctttt ctctgtctga   3000
ccatggcaac aaagagcagc tgacggtgat cagggccact gtgtgcgact gccatggcca   3060
tgtcgaaacc tgccctggac cctggaaggg aggtttcatc ctccctgtgc tggggctgt    3120
cctggctctg ctgttcctcc tgctggtgct gctttgttg gtgagaaaga gcggaagat    3180
caaggagccc ctcctactcc cagaagatga cacccgtgac aacgtcttct actatggcga   3240
```

-continued

```
agaggggggt ggcgaagagg accaggacta tgacatcacc cagctccacc gaggtctgga      3300
ggccaggccg gaggtggttc tccgcaatga cgtggcacca accatcatcc cgacacccat      3360
gtaccgtcct cggccagcca acccagatga aatcggcaac tttataattg agaacctgaa      3420
ggcggctaac acagacccca cagccccgcc ctacgacacc ctcttggtgt tcgactatga      3480
gggcagcggc tccgacgccg cgtccctgag ctccctcacc tcctccgcct ccgaccaaga      3540
ccaagattac gattatctga acgagtgggg cagccgcttc aagaagctgg cagacatgta      3600
cggtggcggg gaggacgact aggcggcctg cctgcagggc tggggaccaa acgtcaggcc      3660
acagagcatc tccaagggg t ctcagttccc ccttcagctg aggacttcgg agcttgtcag     3720
gaagtggccg tagcaacttg gcggagacag gctatgagtc tgacgttaga gtggtggctt      3780
ccttagcctt tcaggatgga ggaatgtggg cagtttgact tcagcactga aaacctctcc      3840
acctgggcca gggttgcctc agaggccaag tttccagaag cctcttacct gccgtaaaat      3900
gctcaaccct gtgtcctggg cctgggcctg ctgtgactga cctacagtgg actttctctc      3960
tggaatggaa ccttcttagg cctcctggtg caacttaatt tttttttta atgctatctt      4020 caaaacgtta gagaaagttc ttcaaaagtg cagcccagag ctgctgggcc cactggccgt      4080
cctgcatttc tggtttccag accccaatgc ctcccattcg gatggatctc tgcgtttta      4140 tactgagtgt gcctaggttg cccttattt tttatttcc ctgttgcgtt gctatagatg       4200
aagggtgagg acaatcgtgt atatgtacta gaacttttt attaaagaaa cttttcccag      4260
aggtgcctgg ggagtg                                                     4276
```

<210> SEQ ID NO 2
<211> LENGTH: 829
<212> TYPE: PRT
<213> ORGANISM: Homo sapiens
<220> FEATURE:
<223> OTHER INFORMATION: placental cadherin, P-cadherin, CDH3

<400> SEQUENCE: 2

```
Met Gly Leu Pro Arg Gly Pro Leu Ala Ser Leu Leu Leu Leu Gln Val
  1               5                  10                  15

Cys Trp Leu Gln Cys Ala Ala Ser Glu Pro Cys Arg Ala Val Phe Arg
             20                  25                  30

Glu Ala Glu Val Thr Leu Glu Ala Gly Gly Ala Glu Gln Glu Pro Gly
         35                  40                  45

Gln Ala Leu Gly Lys Val Phe Met Gly Cys Pro Gly Gln Glu Pro Ala
     50                  55                  60

Leu Phe Ser Thr Asp Asn Asp Asp Phe Thr Val Arg Asn Gly Glu Thr
 65                  70                  75                  80

Val Gln Glu Arg Arg Ser Leu Lys Glu Arg Asn Pro Leu Lys Ile Phe
                 85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
```

```
                    180                 185                 190
Ala Ser Val Glu Asp Pro Met Asn Ile Ser Ile Ile Val Thr Asp Gln
            195                 200                 205

Asn Asp His Lys Pro Lys Phe Thr Gln Asp Thr Phe Arg Gly Ser Val
        210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
        290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
            355                 360                 365

Met Gly Gly Asp Asp Gly Asp His Phe Thr Ile Thr Thr His Pro Glu
        370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
        435                 440                 445

Val Gln Glu Gly Ile Pro Thr Gly Glu Pro Val Cys Val Tyr Thr Ala
        450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
        515                 520                 525

Thr Gly Thr Gly Thr Leu Leu Leu Thr Leu Ile Asp Val Asn Asp His
        530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575

Ser Pro Phe Gln Ala Gln Leu Thr Asp Ser Asp Ile Tyr Trp Thr
            580                 585                 590

Ala Glu Val Asn Glu Glu Gly Asp Thr Val Val Leu Ser Leu Lys Lys
        595                 600                 605
```

```
Phe Leu Lys Gln Asp Thr Tyr Asp Val His Leu Ser Leu Ser Asp His
        610                 615                 620
Gly Asn Lys Glu Gln Leu Thr Val Ile Arg Ala Thr Val Cys Asp Cys
625                 630                 635                 640
His Gly His Val Glu Thr Cys Pro Gly Pro Trp Lys Gly Gly Phe Ile
                    645                 650                 655
Leu Pro Val Leu Gly Ala Val Leu Ala Leu Leu Phe Leu Leu Leu Val
                660                 665                 670
Leu Leu Leu Leu Val Arg Lys Arg Lys Ile Lys Glu Pro Leu Leu
            675                 680                 685
Leu Pro Glu Asp Asp Thr Arg Asp Asn Val Phe Tyr Tyr Gly Glu Glu
        690                 695                 700
Gly Gly Gly Glu Glu Asp Gln Asp Tyr Asp Ile Thr Gln Leu His Arg
705                 710                 715                 720
Gly Leu Glu Ala Arg Pro Glu Val Val Leu Arg Asn Asp Val Ala Pro
                    725                 730                 735
Thr Ile Ile Pro Thr Pro Met Tyr Arg Pro Arg Pro Ala Asn Pro Asp
                740                 745                 750
Glu Ile Gly Asn Phe Ile Ile Glu Asn Leu Lys Ala Ala Asn Thr Asp
            755                 760                 765
Pro Thr Ala Pro Pro Tyr Asp Thr Leu Leu Val Phe Asp Tyr Glu Gly
        770                 775                 780
Ser Gly Ser Asp Ala Ala Ser Leu Ser Ser Leu Thr Ser Ser Ala Ser
785                 790                 795                 800
Asp Gln Asp Gln Asp Tyr Asp Tyr Leu Asn Glu Trp Gly Ser Arg Phe
                    805                 810                 815
Lys Lys Leu Ala Asp Met Tyr Gly Gly Gly Glu Asp Asp
                820                 825

<210> SEQ ID NO 3
<211> LENGTH: 654
<212> TYPE: PRT
<213> ORGANISM: Artificial
<220> FEATURE:
<223> OTHER INFORMATION: placental cadherin, P-cadherin, CDH3 antigen
      for anti-CDH3 antibody, CDH3 transmembrane and
      extracellular domains

<400> SEQUENCE: 3

Met Gly Leu Pro Arg Gly Pro Leu Ala Ser Leu Leu Leu Leu Gln Val
1               5                   10                  15
Cys Trp Leu Gln Cys Ala Ala Ser Glu Pro Cys Arg Ala Val Phe Arg
            20                  25                  30
Glu Ala Glu Val Thr Leu Glu Ala Gly Gly Ala Glu Gln Glu Pro Gly
        35                  40                  45
Gln Ala Leu Gly Lys Val Phe Met Gly Cys Pro Gly Gln Glu Pro Ala
    50                  55                  60
Leu Phe Ser Thr Asp Asn Asp Asp Phe Thr Val Arg Asn Gly Glu Thr
65                  70                  75                  80
Val Gln Glu Arg Arg Ser Leu Lys Glu Arg Asn Pro Leu Lys Ile Phe
                85                  90                  95
Pro Ser Lys Arg Ile Leu Arg Arg His Lys Arg Asp Trp Val Val Ala
            100                 105                 110
Pro Ile Ser Val Pro Glu Asn Gly Lys Gly Pro Phe Pro Gln Arg Leu
        115                 120                 125
Asn Gln Leu Lys Ser Asn Lys Asp Arg Asp Thr Lys Ile Phe Tyr Ser
    130                 135                 140
```

-continued

```
Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
            165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Val Thr Asp Gln
        195                 200                 205

Asn Asp His Lys Pro Lys Phe Thr Gln Asp Thr Phe Arg Gly Ser Val
210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
        355                 360                 365

Met Gly Gly Asp Asp Gly Asp His Phe Thr Ile Thr Thr His Pro Glu
370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
        435                 440                 445

Val Gln Glu Gly Ile Pro Thr Gly Glu Pro Val Cys Val Tyr Thr Ala
450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
        515                 520                 525

Thr Gly Thr Gly Thr Leu Leu Leu Thr Leu Ile Asp Val Asn Asp His
530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
```

```
                565                 570                 575
Ser Pro Phe Gln Ala Gln Leu Thr Asp Asp Ser Asp Ile Tyr Trp Thr
            580                 585                 590

Ala Glu Val Asn Glu Glu Gly Asp Thr Val Val Leu Ser Leu Lys Lys
        595                 600                 605

Phe Leu Lys Gln Asp Thr Tyr Asp Val His Leu Ser Leu Ser Asp His
    610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly
            645                 650
```

<210> SEQ ID NO 4
<211> LENGTH: 34
<212> TYPE: DNA
<213> ORGANISM: Artificial
<220> FEATURE:
<223> OTHER INFORMATION: synthetic PCR amplification 5' primer
      MuIgV-H5'-B for anti-CDH3 monoclonal antibody variable region
      heavy chain, primerVH5'

<400> SEQUENCE: 4
gggaattcat graatgsasc tgggtywtyc tctt                              34

<210> SEQ ID NO 5
<211> LENGTH: 39
<212> TYPE: DNA
<213> ORGANISM: Artificial
<220> FEATURE:
<223> OTHER INFORMATION: synthetic PCR amplification 5' primer
      MuIg kappa V-L5'-G for anti-CDH3 monoclonal antibody
      variable region light chain of Clone #6, primerVL5'-1

<400> SEQUENCE: 5
actagtcgac atgaagttgc ctgttaggct gttggtgct                         39

<210> SEQ ID NO 6
<211> LENGTH: 39
<212> TYPE: DNA
<213> ORGANISM: Artificial
<220> FEATURE:
<223> OTHER INFORMATION: synthetic PCR amplification 5' primer
      MuIg kappa V-L5'-G for anti-CDH3 monoclonal antibody
      variable region light chain of Clone #6, primerVL5'-2

<400> SEQUENCE: 6
actagtcgac atggatttwc argtgcagat twtcagctt                         39

<210> SEQ ID NO 7
<211> LENGTH: 37
<212> TYPE: DNA
<213> ORGANISM: Artificial
<220> FEATURE:
<223> OTHER INFORMATION: synthetic PCR amplification 5' primer
      MuIg kappa V-L5'-G for anti-CDH3 monoclonal antibody
      variable region light chain of Clone #6, primerVL5'-3

<400> SEQUENCE: 7
actagtcgac atggtyctya tvtccttgct gttctgg                           37

<210> SEQ ID NO 8
<211> LENGTH: 37
<212> TYPE: DNA
<213> ORGANISM: Artificial
<220> FEATURE:
<223> OTHER INFORMATION: synthetic PCR amplification 3' primer -continued MuIgGV-H3'-2 for anti-CDH3 monoclonal antibody
variable region light chain of Clone #6, primerVL5'-4
<220> FEATURE:
<223> OTHER INFORMATION: synthetic PCR amplification 3' primer

<400> SEQUENCE: 8
actagtcgac atggtyctya tvttrctgct gctatgg                              37

<210> SEQ ID NO 9
<211> LENGTH: 35
<212> TYPE: DNA
<213> ORGANISM: Artificial
<220> FEATURE:
<223> OTHER INFORMATION: synthetic PCR amplification 3' primer
      MuIgGV-H3'-2 for anti-CDH3 monoclonal antibody
      variable region heavy chain, primerVH3'
<220> FEATURE:
<221> NAME/KEY: MOD-RES
<222> LOCATION: (30)..(30)
<223> OTHER INFORMATION: n = i

<400> SEQUENCE: 9
cccaagcttc cagggrccar kggataracn grtgg                               35

<210> SEQ ID NO 10
<211> LENGTH: 30
<212> TYPE: DNA
<213> ORGANISM: Artificial
<220> FEATURE:
<223> OTHER INFORMATION: synthetic PCR amplification 3' primer
      MuIgGV-H3'-2 for anti-CDH3 monoclonal antibody
      variable region light chain, primerVL3'

<400> SEQUENCE: 10
cccaagctta ctggatggtg ggaagatgga                                     30

<210> SEQ ID NO 11
<211> LENGTH: 118
<212> TYPE: PRT
<213> ORGANISM: Artificial
<220> FEATURE:
<223> OTHER INFORMATION: synthetic anti-CDH3 monoclonal antibody Clone
      #6 H-chain variable region (except for signal sequence), VH

<400> SEQUENCE: 11

Gln Val Gln Leu Gln Gln Pro Gly Ala Glu Leu Val Lys Pro Gly Thr
1               5                   10                  15

Ser Val Lys Leu Ser Cys Lys Ser Ser Gly Tyr Thr Phe Thr Ser Tyr
            20                  25                  30

Trp Ile His Trp Val Lys Gln Arg Pro Gly His Gly Leu Glu Trp Ile
        35                  40                  45

Gly Glu Ile Asp Pro Ser Asp Asn Tyr Thr Tyr Tyr Asn Gln Asn Phe
    50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Glu Asp Ser Ala Val Phe Tyr Cys
                85                  90                  95

Ala Arg Ser Gly Tyr Gly Asn Leu Phe Val Tyr Trp Gly Gln Gly Thr
            100                 105                 110

Leu Val Thr Val Ser Ala
        115

<210> SEQ ID NO 12
<211> LENGTH: 103
<212> TYPE: PRT

```
<213> ORGANISM: Artificial
<220> FEATURE:
<223> OTHER INFORMATION: synthetic anti-CDH3 monoclonal antibody Clone
      #6 L-chain variable region (except for signal sequence), VL

<400> SEQUENCE: 12

Gln Ile Val Leu Thr Gln Ser Pro Ala Ile Met Ser Ser Ser Pro Gly
1               5                   10                  15

Glu Lys Val Thr Met Ser Cys Ser Ala Thr Ser Ser Val Thr Tyr Met
                20                  25                  30

Tyr Trp Tyr Gln Gln Lys Pro Gly Ser Ser Pro Lys Pro Trp Ile Phe
            35                  40                  45

Arg Thr Ser Asn Leu Ala Ser Gly Val Pro Thr Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln His Tyr His Ile Tyr Pro Arg Thr
                85                  90                  95

Phe Gly Gly Gly Thr Lys Leu
                100

<210> SEQ ID NO 13
<211> LENGTH: 5
<212> TYPE: PRT
<213> ORGANISM: Artificial
<220> FEATURE:
<223> OTHER INFORMATION: synthetic anti-CDH3 monoclonal antibody Clone
      #6 H-chain variable region complementarity region 1
      (CDR1), VH CDR1

<400> SEQUENCE: 13

Ser Tyr Trp Ile His
1               5

<210> SEQ ID NO 14
<211> LENGTH: 17
<212> TYPE: PRT
<213> ORGANISM: Artificial
<220> FEATURE:
<223> OTHER INFORMATION: synthetic anti-CDH3 monoclonal antibody Clone
      #6 H-chain variable region complementarity region 2
      (CDR2), VH CDR2

<400> SEQUENCE: 14

Glu Ile Asp Pro Ser Asp Asn Tyr Thr Tyr Tyr Asn Gln Asn Phe Lys
1               5                   10                  15

Gly

<210> SEQ ID NO 15
<211> LENGTH: 9
<212> TYPE: PRT
<213> ORGANISM: Artificial
<220> FEATURE:
<223> OTHER INFORMATION: synthetic anti-CDH3 monoclonal antibody Clone
      #6 H-chain variable region complementarity region 3
      (CDR3), VH CDR3

<400> SEQUENCE: 15

Ser Gly Tyr Gly Asn Leu Phe Val Tyr
1               5

<210> SEQ ID NO 16
<211> LENGTH: 10
<212> TYPE: PRT
<213> ORGANISM: Artificial
```

```
<220> FEATURE:
<223> OTHER INFORMATION: synthetic anti-CDH3 monoclonal antibody Clone
      #6 L-chain variable region complementarity region 1
      (CDR1), VL CDR1

<400> SEQUENCE: 16

Ser Ala Thr Ser Ser Val Thr Tyr Met Tyr
1               5                   10

<210> SEQ ID NO 17
<211> LENGTH: 7
<212> TYPE: PRT
<213> ORGANISM: Artificial
<220> FEATURE:
<223> OTHER INFORMATION: synthetic anti-CDH3 monoclonal antibody Clone
      #6 L-chain variable region complementarity region 2
      (CDR2), VL CDR2

<400> SEQUENCE: 17

Arg Thr Ser Asn Leu Ala Ser
1               5

<210> SEQ ID NO 18
<211> LENGTH: 9
<212> TYPE: PRT
<213> ORGANISM: Artificial
<220> FEATURE:
<223> OTHER INFORMATION: synthetic anti-CDH3 monoclonal antibody Clone
      #6 L-chain variable region complementarity region 3
      (CDR3), VL CDR3

<400> SEQUENCE: 18

Gln His Tyr His Ile Tyr Pro Arg Thr
1               5

<210> SEQ ID NO 19
<211> LENGTH: 330
<212> TYPE: DNA
<213> ORGANISM: Homo sapiens
<220> FEATURE:
<223> OTHER INFORMATION: human kappa light chain constant region

<400> SEQUENCE: 19
gaattaaaac gtactgttgc tgctccttct gttttatttt ttcctccttc tgatgaacaa      60
ttaaaatctg gtactgcttc tgttgtttgt ttattaaata attttatcc tcgtgaagct     120 aaagttcaat ggaaagttga taatgcttta caatctggta attctcaaga atctgttact    180
gaacaagatt ctaaagattc tacttattct ttatcttcta ctttaacttt atctaaagct    240
gattatgaaa aacataaagt ttatgcttgt gaagttactc atcaaggttt atcttctcct    300
gttactaaat cttttaatcg tggtgaatgt                                     330

<210> SEQ ID NO 20
<211> LENGTH: 990
<212> TYPE: DNA
<213> ORGANISM: Homo sapiens
<220> FEATURE:
<223> OTHER INFORMATION: human IgG1 heavy chain constant region

<400> SEQUENCE: 20
gcctccacca agggcccatc ggtcttcccc ctggcaccct cctccaagag cacctctggg      60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
```

```
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 21
<211> LENGTH: 110
<212> TYPE: PRT
<213> ORGANISM: Homo sapiens
<220> FEATURE:
<223> OTHER INFORMATION: human kappa light chain constant region

<400> SEQUENCE: 21

```
Glu Leu Lys Arg Thr Val Ala Ala Pro Ser Val Phe Ile Phe Pro Pro
1               5                   10                  15

Ser Asp Glu Gln Leu Lys Ser Gly Thr Ala Ser Val Val Cys Leu Leu
            20                  25                  30

Asn Asn Phe Tyr Pro Arg Glu Ala Lys Val Gln Trp Lys Val Asp Asn
        35                  40                  45

Ala Leu Gln Ser Gly Asn Ser Gln Glu Ser Val Thr Glu Gln Asp Ser
    50                  55                  60

Lys Asp Ser Thr Tyr Ser Leu Ser Ser Thr Leu Thr Leu Ser Lys Ala
65                  70                  75                  80

Asp Tyr Glu Lys His Lys Val Tyr Ala Cys Glu Val Thr His Gln Gly
                85                  90                  95

Leu Ser Ser Pro Val Thr Lys Ser Phe Asn Arg Gly Glu Cys
            100                 105                 110
```

<210> SEQ ID NO 22
<211> LENGTH: 330
<212> TYPE: PRT
<213> ORGANISM: Homo sapiens
<220> FEATURE:
<223> OTHER INFORMATION: human IgG1 heavy chain constant region

<400> SEQUENCE: 22

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                    65                  70                  75                  80
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 39
<212> TYPE: DNA
<213> ORGANISM: Artificial
<223> OTHER INFORMATION: synthetic chimeric mouse/human anti-CDH3
      monoclonal antibody ch-#6 heavy chain variable region PCR
      amplification primer HindIIICDH3#6VH-f

<400> SEQUENCE: 23
aagcttgccg ccaccatgaa atggagctgg gttattctc                         39

<210> SEQ ID NO 24
<211> LENGTH: 30
<212> TYPE: DNA
<213> ORGANISM: Artificial
<223> OTHER INFORMATION: synthetic chimeric mouse/human anti-CDH3
      monoclonal antibody ch-#6 heavy chain variable region PCR
      amplification primer CDH3#6VHCH-r

<400> SEQUENCE: 24
cccttggtgg aggctgcaga gacagtgacc                                   30

<210> SEQ ID NO 25
<211> LENGTH: 42
<212> TYPE: DNA
```

<213> ORGANISM: Artificial
<223> OTHER INFORMATION: synthetic chimeric mouse/human anti-CDH3
monoclonal antibody ch-#6 light chain variable region PCR
amplification primer HindIIICDH3#6VL-f

<400> SEQUENCE: 25
aagcttgccg ccaccatgga tttacaggtg cagattatca gc          42

<210> SEQ ID NO 26
<211> LENGTH: 29
<212> TYPE: DNA
<213> ORGANISM: Artificial
<220> FEATURE:
<223> OTHER INFORMATION: CDH3#6VLkappa-r
<223> OTHER INFORMATION: synthetic chimeric mouse/human anti-CDH3
monoclonal antibody ch-#6 light chain variable region PCR
amplification primer CDH3#6VLkappa-r

<400> SEQUENCE: 26
cgttttaatt ccagcttggt gcctccacc                          29

<210> SEQ ID NO 27
<211> LENGTH: 29
<212> TYPE: DNA
<213> ORGANISM: Artificial
<223> OTHER INFORMATION: synthetic chimeric mouse/human anti-CDH3
monoclonal antibody ch-#6 human IgG1 constant region PCR
amplification primer CDH3#6VHCH-f

<400> SEQUENCE: 27
ctctgcagcc tccaccaagg gcccatcgg                          29

<210> SEQ ID NO 28
<211> LENGTH: 41
<212> TYPE: DNA
<213> ORGANISM: Artificial
<223> OTHER INFORMATION: synthetic chimeric mouse/human anti-CDH3
monoclonal antibody ch-#6 human IgG1 constant region PCR
amplification and overlap extension primer EcoRIIgG1-r

<400> SEQUENCE: 28
ttattagaat tcctatcatt tacccggaga cagggagagg c            41

<210> SEQ ID NO 29
<211> LENGTH: 29
<212> TYPE: DNA
<213> ORGANISM: Artificial
<223> OTHER INFORMATION: synthetic chimeric mouse/human anti-CDH3
monoclonal antibody ch-#6 human kappa constant region PCR
amplification primer CDH3#6VLkappa-f

<400> SEQUENCE: 29
accaagctgg aattaaaacg tactgttgc                          29

<210> SEQ ID NO 30
<211> LENGTH: 51
<212> TYPE: DNA
<213> ORGANISM: Artificial
<223> OTHER INFORMATION: synthetic chimeric mouse/human anti-CDH3
monoclonal antibody ch-#6 human kappa constant region PCR
amplification and overlap extension primer EcoRIKappa-r

<400> SEQUENCE: 30
ttattagaat tcctatcaac attcaccacg attaaaagat ttagtaacag g   51

<210> SEQ ID NO 31
<211> LENGTH: 100
<212> TYPE: DNA

```
<213> ORGANISM: Artificial
<223> OTHER INFORMATION: synthetic chimeric mouse/human anti-CDH3
      monoclonal antibody ch-#6 heavy chain overlap extension PCR
      amplification primer HindIIIB72.3CDH3#6H-f

<400> SEQUENCE: 31
cacgaagctt gccgccacca tggaatggag ctgggtgttc ctgttctttc tgtccgtgac      60
cacaggcgtg cattctcagg tccaactgca gcagcctggg                           100

<210> SEQ ID NO 32
<211> LENGTH: 100
<212> TYPE: DNA
<213> ORGANISM: Artificial
<223> OTHER INFORMATION: synthetic chimeric mouse/human anti-CDH3
      monoclonal antibody ch-#6 light chain overlap extension PCR
      amplification primer HindIIIB72.3CDH3#6L-f

<400> SEQUENCE: 32
acgaagcttg ccgccaccat gtctgtgcct acccaggtgc tgggactgct gctgctgtgg      60
ctgacagacg cccgctgtca aattgttctc acccagtctc                           100
```